US01209457B2

(12) United States Patent
Tian et al.

(10) Patent No.: US 12,094,577 B2
(45) Date of Patent: Sep. 17, 2024

(54) METHOD AND SYSTEM FOR DETECTING AMOUNT OF SHALE OIL BASED ON OCCURRENCE STATE

(71) Applicant: Northeast Petroleum University, Heilongjiang (CN)

(72) Inventors: Shansi Tian, Daqing (CN); Bo Liu, Daqing (CN); Fang Zeng, Daqing (CN); Xiaofei Fu, Daqing (CN); Ya'ao Chi, Daqing (CN); Tong Wu, Daqing (CN); Haiyang Yan, Daqing (CN)

(73) Assignee: NORTHEAST PETROLEUM UNIVERSITY, Heilongjiang (CN)

( * ) Notice: Subject to any disclaimer, the term of this patent is extended or adjusted under 35 U.S.C. 154(b) by 1043 days.

(21) Appl. No.: 17/017,121

(22) Filed: Sep. 10, 2020

(65) Prior Publication Data
US 2022/0059191 A1 Feb. 24, 2022

(30) Foreign Application Priority Data
Aug. 24, 2020 (CN) .......................... 202010856523.1

(51) Int. Cl.
*G16C 10/00* (2019.01)
*G16C 60/00* (2019.01)

(52) U.S. Cl.
CPC .............. *G16C 10/00* (2019.02); *G16C 60/00* (2019.02)

(58) Field of Classification Search
CPC ................................ G16C 10/00; G16C 60/00
See application file for complete search history.

(56) References Cited

U.S. PATENT DOCUMENTS

| 2010/0161302 A1* | 6/2010 | Walters | ........... E21B 43/24 703/12 |
| 2015/0212235 A1* | 7/2015 | Barwise | ........... G01V 20/00 703/2 |
| 2020/0173902 A1* | 6/2020 | Wang | ........... G01N 15/08 |
| 2020/0408090 A1* | 12/2020 | Kadayam Viswanathan | ........... E21B 49/02 |

FOREIGN PATENT DOCUMENTS

CN 110895254 A * 3/2020 ........... G01N 24/081

OTHER PUBLICATIONS

Colin Bousige et al.; "Realistic molecular model of kerogen's nanostructure"; Nature Materials | vol. 15 | May 2016 (Year: 2016).*

(Continued)

*Primary Examiner* — Rehana Perveen
*Assistant Examiner* — Nupur Debnath
(74) *Attorney, Agent, or Firm* — Cozen O'Connor

(57) ABSTRACT

A method and system for detecting an amount of shale oil based on an occurrence state, wherein an occurrence-state-based shale oil quantification model is established in accordance with a kerogen swelled amount, an amount of kerogen absorbed oil, an amount of free oil in an organic pore, an amount of adsorbed oil by an inorganic mineral and an amount of free oil in an inorganic pore, and detects an amount of shale oil is detected in accordance with the occurrence-state-based shale oil quantification model, such that the accuracy of the evaluation of shale oil mobility is improved.

9 Claims, 12 Drawing Sheets

(56) References Cited

OTHER PUBLICATIONS

Shansi Tian et al.; "Molecular Simulation of Oil Mixture Adsorption Character in Shale System"; Journal of Nanoscience and Nanotechnology; vol. 17, 6198-6209, 2017 (Year: 2017).*
Shansi Tian et al.; "Understanding Model Crude Oil Component Interactions on Kaolinite Silicate and Aluminol Surfaces: Toward Improved Understanding of Shale Oil Recovery"; Energy Fuels 2018, 32, 1155-1165 (Year: 2018).*
J. A. Piedrahita et al.; "Models for Calculating Organic and Inorganic Porosities in Shale Oil Reservoirs"; SPE-185591-MS (Year: 2017).*
Jan Goral et al.; "Pore system characterization of organic-rich shales using nanoscale-resolution 3D imaging"; Fuel 258 (2019) 116 (Year: 2019).*
Manas Pathak et al.; "Kerogen Swelling and Confinement: Its implication on Fluid Thermodynamic Properties in Shales"; Scientific Reports | 7: 12530; (Year: 2017).*

* cited by examiner

METHOD AND SYSTEM FOR DETECTING AMOUNT OF SHALE OIL BASED ON OCCURRENCE STATE

BACKGROUND OF THE INVENTION

1. Field of the Invention

The present invention relates to the technical field of petroleum geology and exploration, in particular to a method and system for detecting an amount of shale oil based on an occurrence state.

2. Description of the Related Art

Shale has the potential to become an oil reservoir. The effective mobility and flow of oil in shale are related to the size, structure, distribution and connectivity of the pore throat in the shale, as well as the liquid-solid interactions and the occurrence states (such as adsorbed, free and dissolved) and mechanisms of oil in the reservoir. Therefore, the effective mobility and flow of shale oil are further related to the composition, types and physical properties (such as viscosity and density) of shale oil.

Due to the complexity of kerogen (with complex elements and functional groups), two-dimensional carbon materials such as graphene are usually used to replace kerogen to carry out molecular dynamics simulation on the interaction of shale oil on the surface of kerogen. However, since graphene is a simple two-dimensional carbon material, it is not feasible to be used to study the adsorption of shale oil. The shale oil adsorption system used for molecular dynamics simulation is usually less than 20 nm while the pore size of the shale reservoir is dominantly greater than 20 nm. Such a small adsorption system is difficult to apply to the adsorption of shale oil. The occurrence states of shale oil (dissolved, swelling, adsorbed and free) and the occurrence mechanisms of shale oil (the proportions of the occurrence states, the pore size for occurrence and the mutual transformation conditions) are closely related to the mobility of shale oil. Due to the low water content in shale and the extremely low solubility of oil in water, the dissolved shale oil is ignored in the study of shale oil occurrence. The swelling shale oil occurs in the organic matter, where shale oil molecules are "surrounded" by kerogen molecules, making it the most difficult for the swelling shale oil to flow. The adsorbed oil is adsorbed on the surface of the organic matter and mineral particles in a "solid-like" state, and its mobility is superior to that of the swelling shale oil. The free shale oil is not subjected to the adsorption by kerogen and mineral particles, and is the most easy to flow. The amount of the free shale oil in shale matters the effective exploration and development of rich shale oil resources, and the quantitative evaluation of shale oil occurring in different states is a key issue that needs to be solved urgently.

SUMMARY OF THE INVENTION

It is an object of the present invention to provide a method and system for detecting an amount of shale oil based on an occurrence which establishes an amount evolution model of shale oil with different occurrence states in shale such that the accuracy of shale oil mobility evaluation is improved.

This and other objects and advantages are achieved in accordance with the invention by a method for detecting an amount of shale oil based on an occurrence state that includes: obtaining a kerogen molecular model, loading the kerogen molecular model into a pore formed by a graphene lamellar structure, and performing energy minimization (EM), relaxation, simulated annealing and shale oil molecular loading in sequence to obtain a swelling and adsorption model of shale oil in kerogen; assigning a value to force fields of a shale oil molecule and a kerogen molecule in the kerogen shale oil swelling and adsorption model to determine kerogen and shale oil density curves; calculating a kerogen swelled amount according to the kerogen and shale oil density curves;

determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area; determining a specific surface area of kerogen according to a number and diameter of organic pores in a shale sample; multiplying the amount of kerogen adsorbed oil per unit area by the specific surface area of kerogen to obtain an amount of kerogen adsorbed oil;

obtaining a kerogen swelling capacity and an organic pore volume formed by kerogen generated oil and gas, and calculating an organic pore volume corresponding to organic carbon according to the kerogen swelling capacity and the organic pore volume formed by kerogen generated oil and gas; multiplying a difference between the organic pore volume corresponding to the organic carbon and a volume of a kerogen adsorbed oil phase by a shale oil density, to obtain an amount of free oil in an organic pore, where the volume of the kerogen adsorbed oil phase is a ratio of the amount of kerogen adsorbed oil to a density thereof;

dividing the shale sample into a first shale sample and a second shale sample, and extracting the first shale sample by using chloroform to obtain a total content of shale oil in the shale; sequentially enriching kerogen from the second shale sample, oven-drying, extracting with chloroform and comparing a mass of kerogen to obtain an amount of oil in an organic matter of the shale sample; determining an amount of oil in an inorganic mineral according to the total content of shale oil in the shale and the amount of oil in the organic matter of the shale sample;

loading compound composition of shale oil into a kaolinite pore to obtain a kaolinite pore-shale oil model, and performing molecular dynamics simulation on the kaolinite pore-shale oil model to obtain a density curve of shale oil in the kaolinite pore; determining a surface oil adsorption capacity per unit area of kaolinite according to the density curve of shale oil in the kaolinite pore and a surface area of the kaolinite pore-shale oil model; determining a specific surface area of the inorganic mineral in the shale sample according to a number of inorganic pores in the shale sample and a surface area of an inorganic pore in the shale sample; multiplying the surface oil adsorption capacity per unit area of kaolinite by the specific surface area of the inorganic mineral in the shale sample to obtain an amount of adsorbed oil by the inorganic mineral in the shale;

determining a difference between the amount of oil in the inorganic mineral and the amount of adsorbed oil by the inorganic mineral in the shale as an amount of free oil in the inorganic pore; and establishing an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detecting an amount of shale oil according to the occurrence-state-based shale oil quantification model.

Optionally, the step of obtaining a kerogen molecular model, loading the kerogen molecular model into a pore formed by a graphene lamellar structure, and performing EM, relaxation, simulated annealing and shale oil molecular loading in sequence to obtain a swelling and adsorption model of shale oil in kerogen specifically includes:

loading the kerogen molecular model into a pore formed by a graphene lamellar structure, then performing EM, and performing relaxation at 75° C. under 20 MPa for 200 ps to obtain a compacted kerogen aggregate model;

subjecting the compacted kerogen aggregate model to 200 ps relaxation warming, and performing simulation by using a constant number of particles, pressure, and temperature (NPT) ensemble at 800° C. under normal pressure for 2 ns to obtain a kerogen slit pore; and loading a shale oil molecule into the kerogen slit pore to obtain a swelling and adsorption model of shale oil in kerogen.

Optionally, the step of calculating a kerogen swelled amount according to the kerogen and shale oil density curves specifically includes:

calculating an amount of kerogen swelling oil by $$Q_{oil} = \int_{L_{o1}}^{L_{o2}} S_{model} \cdot \rho_{oil} dL$$

according to the kerogen and shale oil density curves, where, $Q_{oil}$ is the amount of kerogen swelling oil; $L_{o1}$ is an initial position of an intersection between the kerogen density curve and the shale oil density curve; $l_{o2}$ is a cut-off position of the intersection between the kerogen density curve and the shale oil density curve; $S_{model}$ is a cross-sectional area of the kerogen shale oil swelling and adsorption model; $\rho_{oil}$ is the shale oil density curve;

obtaining a mass of kerogen, and dividing the amount of kerogen swelling oil by the mass of kerogen to obtain an amount of kerogen swelling oil per unit mass; and calculating a kerogen swelled amount $Q_s$ by $Q_s = Q_w \cdot m_k \cdot f_s$ according to the amount of kerogen swelling oil per unit mass, where $Q_w$ is the amount of kerogen swelling oil per unit mass; $m_k$ is a kerogen mass corresponding to 1 g of organic carbon; $f_s$ is a swelling ratio reduction coefficient.

Optionally, the step of determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area specifically includes:

calculating an amount $Q_a$ of kerogen adsorbed oil per unit area by:

$$Q_a = (m_{a1} + m_{a2})/(2 \cdot S_{model})$$

where $$m_{a1} = \int_{L1}^{L2} S_{model} \cdot \rho_{oil} dL$$

$$m_{a2} = \int_{L3}^{L4} S_{model} \cdot \rho_{oil} dL$$

where, $m_{a1}$ is an amount of adsorbed oil on a left side wall of kerogen; $L_1$ is a left side position of the intersection between the kerogen density curve and the shale oil density curve; $L_2$ is a left side position of a boundary between an adsorption zone and a free zone of the shale oil density curve; $M_{a2}$ is an amount of adsorbed oil on a right side wall of kerogen; $L_3$ is a right side position of the boundary between the adsorption zone and the free zone of the shale oil density curve; $L_4$ is a right side position of the intersection between the kerogen density curve and the shale oil density curve.

Optionally, the step of calculating an organic pore volume corresponding to organic carbon according to the kerogen swelling capacity and the organic pore volume formed by kerogen generated oil and gas specifically includes:

calculating an organic re volume corresponding to organic carbon by:

$$V_\phi = \begin{cases} [V_f \cdot (1 - F_t) + V_s] \cdot Q_v & \text{If } [V_f \cdot (1 - F_t) + V_s] \cdot Q_v < V_{gh}| \\ V_{gh} & \text{If } [V_f \cdot (1 - F_t) + V_s] \cdot Q_v \geq V_{gh}| \end{cases}$$

where, $V_\emptyset$ is the organic pore volume corresponding to organic carbon, $V_f$ is a volume of a transformable part of kerogen, $F_t$ is a transformation ratio, $V_s$ is a volume of a non-transformable part of kerogen, $Q_v$ is the kerogen swelling capacity, and $V_{gh}$ is the organic pore volume formed by kerogen generated oil and gas.

Optionally, the step of sequentially enriching kerogen from the second shale sample, oven-drying, extracting with chloroform and comparing a mass of kerogen, to obtain an amount of oil in the organic matter of the shale sample specifically includes:

enriching kerogen from the second shale sample to obtain dry kerogen;

oven-drying the dry kerogen to obtain oven-dried kerogen, and determining a mass of the oven-dried kerogen;

extracting the oven-dried kerogen by using chloroform, and determining a mass of the extracted kerogen;

determining a difference between the mass of the oven-dried kerogen and the mass of the extracted kerogen as an amount of oil in the organic matter, and multiplying a ratio of the amount of oil in the organic matter to a weight of the second shale sample by 100 to obtain an amount of oil in the organic matter of the shale sample.

Optionally, the step of determining an amount of oil in an inorganic mineral according to the total content of shale oil in the shale and the amount of oil in the organic matter of the shale sample specifically includes:

subtracting the amount of the oil in the organic matter of the shale sample from the total content of shale oil in the shale to obtain an amount of oil in the inorganic mineral of the shale sample;

fitting a ratio of the amount of oil in the inorganic mineral of the shale sample to the amount of oil in the organic matter of the shale sample and parameters of the shale sample to establish a model for predicting the ratio of the amount of oil in the inorganic mineral of shale to the amount of oil in the organic matter, where the parameters of the shale sample include mineral composition ratios, total organic carbon (TOC), vitrinite reflectance (VR) and porosity;

obtaining an amount of oil in an organic matter of shale to be detected; and using the prediction model to determine an amount of oil in an inorganic mineral of the shale to be detected according to the amount of oil in the organic matter of the shale to be detected;

where, the prediction model is expressed by:

$$W_{inorganic/organic} = \frac{1}{\sqrt{2\pi} \cdot (d_1 + d_2)} (M_{TOC} \cdot TOC + M_q \cdot \text{Quanrtz} + M_c \cdot \text{Clay} + M_o \cdot \text{Other}) \cdot$$
$$\text{EXP}\left[-\left(\frac{\ln R_o - a}{d_1}\right)^2 - \left(\frac{\ln \Phi - b}{d_2}\right)^2\right]$$

where, $W_{inorganic/organic}$ indicates a ratio of the amount of oil in the inorganic mineral of the shale to the amount of oil in the organic matter of the shale sample; TOC indicates total organic carbon; $M_{TOC}$ indicates a TOC coefficient; Quartz indicates a quartz ratio; $M_q$ indicates a quartz ratio coefficient; Clay indicates a clay mineral ratio; Me indicates a clay mineral ratio coefficient; Other indicates other ratio, such as a carbonate mineral ratio; $M_o$ indicates other mineral ratio coefficient, such as a carbonate mineral ratio coefficient; $R_o$ indicates VR; a indicates a first VR coefficient; $d_1$ indicates a second VR coefficient; $\Phi$ indicates porosity; b indicates a first porosity coefficient; $d_2$ indicates a second porosity coefficient.

Optionally, the step of performing molecular dynamics simulation on the kaolinite pore-shale oil model to obtain a density curve of shale oil in the kaolinite pore specifically includes:

performing EM and relaxation on the kaolinite pore-shale oil model; and performing molecular dynamics simulation on the relaxed kaolinite pore-shale oil model by using the NPT ensemble at a preset temperature and pressure to obtain a density curve of shale oil in the kaolinite pore.

Optionally, the step of determining a surface oil adsorption capacity per unit area of kaolinite according to the density curve of shale oil in the kaolinite pore and a surface area of the kaolinite pore-shale oil model specifically includes:

determining a surface oil adsorption capacity per unit area of kaolinite according to the following formula:

$$c = (c_{ada-a} + c_{ads-a})/2$$

$$c_{ada-a} = \frac{m_{ada}}{A_{ada}} = \frac{\int_{L_5}^{L_6} s_{model}^{(1)} \cdot \rho_{oil}^{(1)} dL}{A_{ada}}$$

$$c_{ads-a} = \frac{m_{ads}}{A_{ads}} = \frac{\int_{L_7}^{L_8} s_{model}^{(1)} \cdot \rho_{oil}^{(1)} dL}{A_{ads}}$$

where, c represents the surface oil absorption capacity per unit area of kaolinite; $C_{ada-a}$ represents a surface oil absorption capacity per unit area of an aluminum-oxygen octahedron; $C_{ads-a}$ represents a surface oil absorption capacity per unit area of a silicon-oxygen tetrahedron; $m_{ada}$ represents a surface adsorption mass of the aluminum-oxygen octahedron; $m_{ads}$ represents a surface adsorption mass of the silicon-oxygen tetrahedron; $A_{ada}$ represents a surface area of the aluminum-oxygen octahedron in the kaolinite pore-shale oil model; $A_{ads}$ represents a surface area of the silicon-oxygen tetrahedron in the kaolinite pore-shale oil model; $s_{model}^{(1)}$ represents a cross-sectional area of the kaolinite pore-shale oil model; $\rho_{oil}^{(1)}$ represents a density curve of shale oil in the kaolinite pore; $L_5$ represents an initial position of the density curve of shale oil in the kaolinite pore; $L_6$ represents a cut-off position of a surface adsorption layer of the aluminum-oxygen octahedron; $L_7$ represents a position where an adsorbed phase separates from a free phase on a surface of the aluminum-oxygen octahedron; $L_8$ represents a cut-off position of the density curve of shale oil in the kaolinite pore.

A system for detecting an amount of shale oil based on an occurrence state, along with a processor an memory, includes:

a kerogen swelled amount determination module, for obtaining a kerogen molecular model, loading the kerogen molecular model into a pore formed by a graphene lamellar structure, and performing EM, relaxation, simulated annealing and shale oil molecular loading in sequence to obtain a swelling and adsorption model of shale oil in kerogen; assigning a value to force fields of a shale oil molecule and a kerogen molecule in the kerogen shale oil swelling and adsorption model to determine kerogen and shale oil density curves; calculating a kerogen swelled amount according to the kerogen and shale oil density curves;

a kerogen adsorbed oil amount determination module, for determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area; determining a specific surface area of kerogen according to a number and diameter of organic pores in a shale sample; multiplying the amount of kerogen adsorbed oil per unit area by the specific surface area of kerogen to obtain an amount of kerogen adsorbed oil;

an organic pore free oil amount determination module, for obtaining a kerogen swelling capacity and an organic pore volume formed by kerogen generated oil and gas, and calculating an organic pore volume corresponding to organic carbon according to the kerogen swelling capacity and the organic pore volume formed by kerogen generated oil and gas; multiplying a difference between the organic pore volume corresponding to the organic carbon and a volume of a kerogen adsorbed oil phase by a shale oil density, to obtain an amount of free oil in an organic pore, where the volume of the kerogen adsorbed oil phase is a ratio of the amount of kerogen adsorbed oil to a density thereof;

an inorganic mineral oil amount determination module, for dividing the shale sample into a first shale sample and a second shale sample, and extracting the first shale sample by using chloroform to obtain a total content of shale oil in the shale; sequentially enriching kerogen from the second shale sample, oven-drying, extracting with chloroform and comparing a mass of kerogen to obtain an amount of oil in an organic matter of the shale sample; determining an amount of oil in an inorganic mineral according to the total content of shale oil in the shale and the amount of oil in the organic matter of the shale sample;

an inorganic mineral adsorbed oil amount determination module, for loading compound composition of shale oil into a kaolinite pore to obtain a kaolinite pore-shale oil model, and performing molecular dynamics simulation on the kaolinite pore-shale oil model to obtain a density curve of shale oil in the kaolinite pore; determining a surface oil adsorption capacity per unit area of kaolinite according to the density curve of shale oil in the kaolinite pore and a surface area of the kaolinite pore-shale oil model; determining a specific surface area of the inorganic mineral in the shale sample according to a number of inorganic pores in the shale sample and a surface area of an inorganic pore in the shale sample; multiplying the surface oil adsorption capacity per unit area of kaolinite by the specific surface area of the inorganic mineral in the shale sample to obtain an amount of adsorbed oil by the inorganic mineral in the shale;

an inorganic pore free oil amount determination module, for determining a difference between the amount of oil in the inorganic mineral and the amount of adsorbed oil by the inorganic mineral in the shale as an amount of free oil in the inorganic pore; and a model establishment module, for establishing an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detecting an amount of shale oil according to the occurrence-state-based shale oil quantification model.

Compared with the prior art, the present invention has the following beneficial effects:

The present invention provides a method and system for detecting an amount of shale oil based on an occurrence state. The present invention establishes an occurrence-state-based shale oil quantification model according to a kerogen swelled amount, an amount of kerogen absorbed oil, an amount of free oil in an organic pore, an amount of adsorbed oil by an inorganic mineral and an amount of free oil in an inorganic pore, and detects an amount of shale oil according to the occurrence-state-based shale oil quantification model. The present invention improves the accuracy of shale oil mobility evaluation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To describe the technical solutions in the examples of the present invention or in the prior art more clearly, the accompanying drawings required for the examples are briefly described below. Apparently, the accompanying drawings in the following description show merely some examples of the present invention, and a person of ordinary skill in the art may still derive other accompanying drawings from these accompanying drawings without creative efforts.

DETAILED DESCRIPTION OF THE EXEMPLARY EMBODIMENTS

The technical solutions in the examples of the present invention are clearly and completely described below with reference to the accompanying drawings in the examples of the present invention. Apparently, the described examples are merely a part rather than all of the examples of the present invention. All other examples obtained by a person of ordinary skill in the art based on the examples of the present invention without creative efforts shall fall within the protection scope of the present invention.

An objective of the present invention is to provide a method and system for detecting an amount of shale oil based on an occurrence state. By establishing an amount evolution model of shale oil with different occurrence states in shale, the present improves the accuracy of shale oil mobility evaluation.

In order to make the above objectives, features and advantages of the present invention more understandable, the present invention will be described in further detail below with reference to the accompanying drawings and detailed examples.

EXAMPLES

Figure 1:
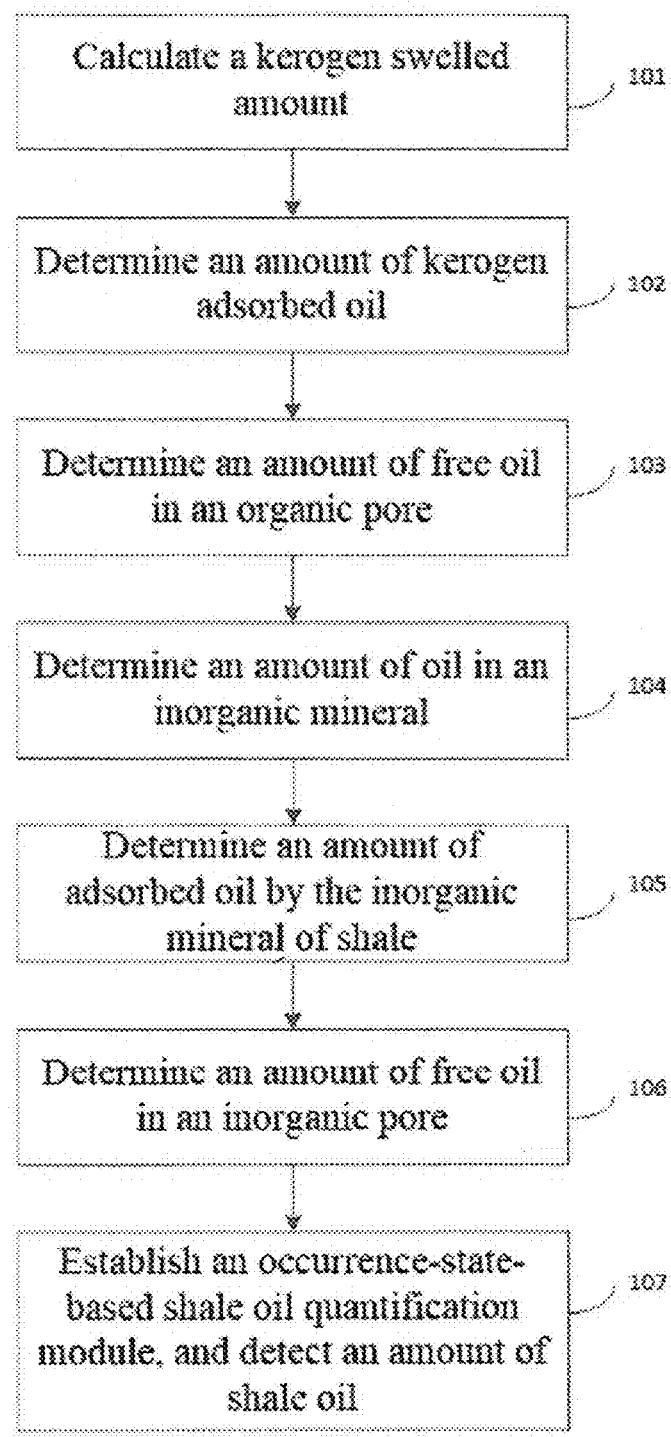
FIG. 1 is a flowchart of a method for detecting an amount of shale oil based on an occurrence state in accordance with an exemplary embodiment of the present invention.

FIG. 1 is a flowchart of a method for detecting an amount of shale oil based on an occurrence state according to an example of the present invention. As shown in FIG. 1, the method for detecting an amount of shale oil based on an occurrence state includes:

Step 101: Obtain a kerogen molecular model, load the kerogen molecular model into a pore formed by a graphene lamellar structure, and perform energy minimization (EM), relaxation, simulated annealing and shale oil molecular loading in sequence to obtain a swelling and adsorption model of shale oil in kerogen; assign a value to force fields of a shale oil molecule and a kerogen molecule in the kerogen shale oil swelling and adsorption model to determine kerogen and shale oil density curves; calculate a kerogen swelled amount according to the kerogen and shale oil density curves.

Figure 2:
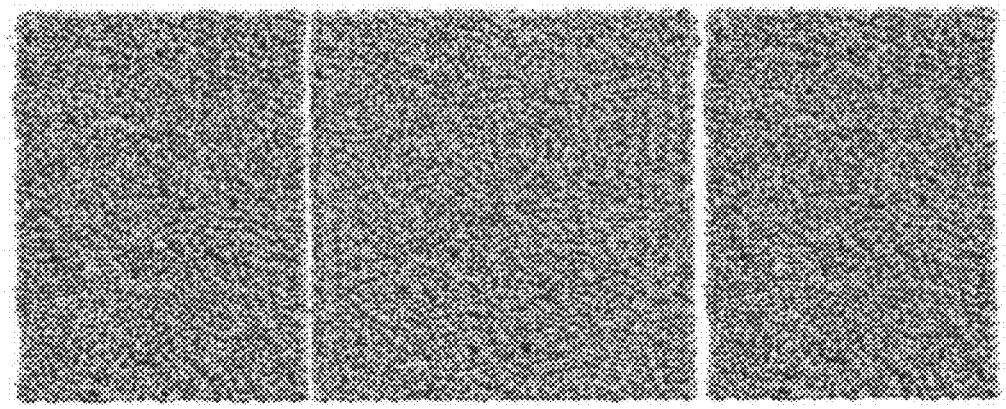
FIG. 2 shows a swelling and adsorption model of shale oil in kerogen in accordance with an exemplary embodiment of the present invention.

A type I kerogen molecular model is established by using Avogadro software, and 100 type II kerogen molecules are loaded by using Packmol software into a slit pore formed by a graphene lamellar structure (approximately 7.38 nm×7.67 nm×0.85 nm). An initial model is subjected to EM by using Gromacs software and to relaxation at 75° C. under 20 MPa for 200 ps by using a constant number of particles, pressure, and temperature (NPT) ensemble, thereby compacting a loose kerogen aggregate model. Then the compacted kerogen aggregate model is warmed by 200 ps relaxation, and the pressure of the system is reduced to normal pressure. Then the entire system is simulated by using the NPT ensemble at 800° C. under normal pressure for 2 ns. Then the system is cooled and pressurized, and the entire system is simulated by using the NPT ensemble at 75° C. under 20 MPa for 2 ns. A shale oil molecule is loaded by using Packmol software into the kerogen slit pore. FIG. 2 shows a kerogen shale oil swelling and adsorption model after loading, which is composed of a double-side kerogen wall model after a simulated annealing process and a middle shale oil model.

Figure 3:
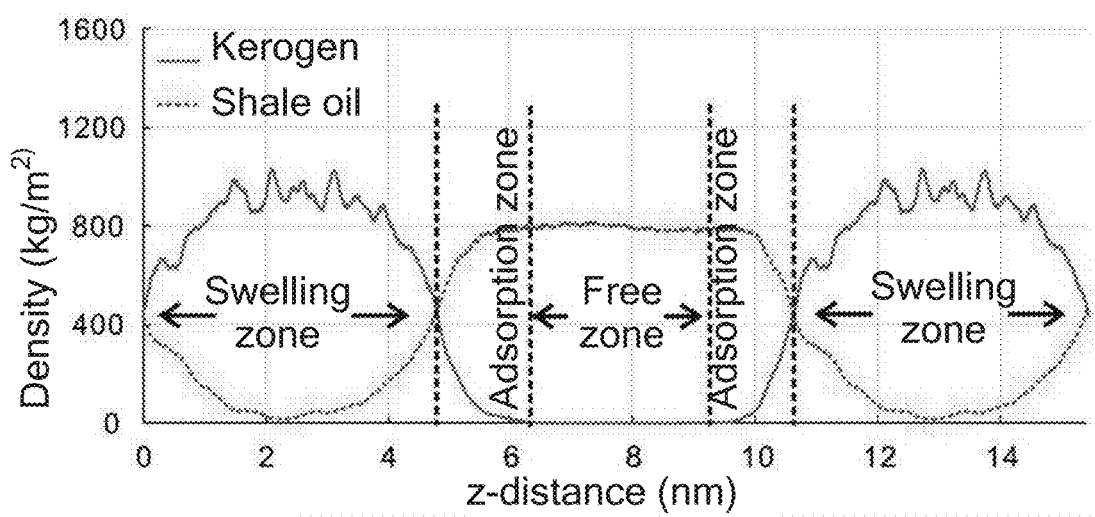
FIG. 3 shows exemplary graphical plots of kerogen and shale oil density curves in accordance with the present invention.

A Chemistry at Harvard Macromolecular Mechanics (CHARMM) 36/CHARMM general (CGenFF) force field is used to assign a value to force fields of the shale oil molecule and the kerogen molecule in the kerogen shale oil swelling and adsorption model. A Lorentz-Berthelot (LB) mixing rule is used to calculate an interaction force between the shale oil molecule and the kerogen molecule. A Particle-Mesh-Ewald (PME) model is used as an electrostatic force model. A van der Waals radius is 1.4 nm. The model after the force field assignment is simulated by using the NPT ensemble of Gromacs software at 75° C. under 20 MPa for 200 ns. Kerogen and shale oil density curves are plotted, as shown in FIG. 3.

An amount of kerogen swelling oil is calculated by $$Q_{oil} = \int_{L_{o1}}^{L_{o2}} S_{model} \cdot \rho_{oil} dL$$

according to the kerogen and shale oil density curves, where, $Q_{oil}$ is the amount of kerogen swelling oil; $L_{o1}$ is a an initial position of an intersection between the kerogen density curve and the shale oil density curve; $L_{o2}$ is a cut-off position of the intersection between the kerogen density curve and the shale oil density curve; $S_{model}$ is a cross-sectional area of the kerogen shale oil swelling and adsorption model; $\rho_{oil}$ is the shale oil density curve.

A mass of kerogen is obtained, and the amount of kerogen swelling oil is divided by the mass of kerogen to obtain an amount $Q_w$ of kerogen swelling oil per unit mass, where the amount of swelling oil in both type I and III kerogen is 161.04 mg/g TOC, and an initial swelling coefficient $Q_{v0}$ is 1.161, dimensionless.

Figure 4A:
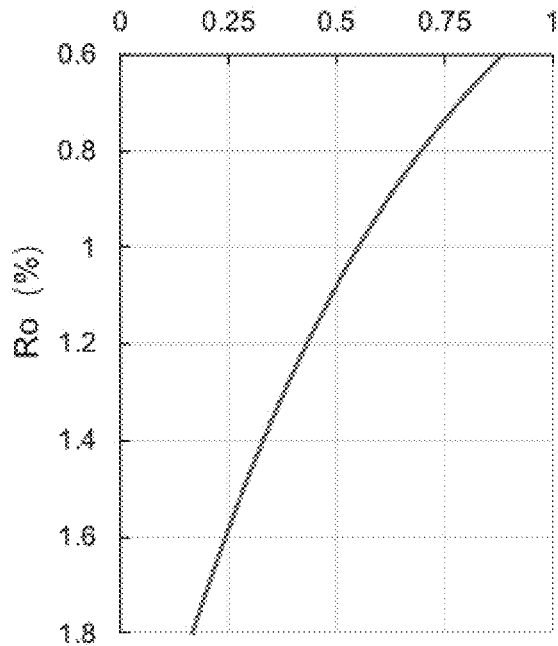
FIGS. 4(a) to 4(d) respectively show exemplary diagrams of a swelling ratio reduction coefficient, a transformation ratio, a kerogen mass and an amount of kerogen swelling oil which evolve with $R_o$ in accordance with the present invention.

Taking the Qing-1 Member in the Songliao Basin as an example, as the shale in the Qing-1 Member is dominated by type I kerogen, the amount of swelling oil in the type I kerogen obtained by the present invention by molecular dynamics simulation is used as an initial swelling amount. Since the ability of oil to swell kerogen decreases continuously with the evolution stage, 1 g of original organic carbon is used to normalize the amount of kerogen swelling oil. The initial swelling amount is multiplied by the mass of type I kerogen in different evolution stages and by a swelling ratio reduction coefficient (FIG. 4*a*) to obtain the amount of swelling oil in type I kerogen in different evolution stages.

The kerogen swelled amount $Q_s$ is calculated by $Q_s = Q_w \cdot m_k \cdot f_s$ according to the amount of kerogen swelling oil per unit mass, where $Q_w$ is the amount of kerogen swelling oil per unit mass, 161.04 mg/g; $m_k$ is a kerogen mass corresponding to 1 g of organic carbon; $f_s$ is a swelling ratio reduction coefficient.

Kerogen mass corresponding to 1 g of original organic carbon:

$$m_k = m_f F_t + m_s = (HI^0/1000) \cdot F_t + (1 - HI^0 \cdot 0.083/100)$$

In the formula, $m_f$ is a mass of a transformable part of kerogen, g; $m_s$ is a mass of a non-transformable part of kerogen, g; $HI^0$ is an original hydrogen index, mg/g TOC; 0.083 is a carbon transformation coefficient of the hydrogen index, dimensionless; $F_t$ is a transformation ratio, dimensionless. The $HI^0$ of type I kerogen in the shale of the Qing-1 Member in the northern Songliao Basin is determined as 750 mg/g TOC according to the geochemical data thereof.

Figure 4B:
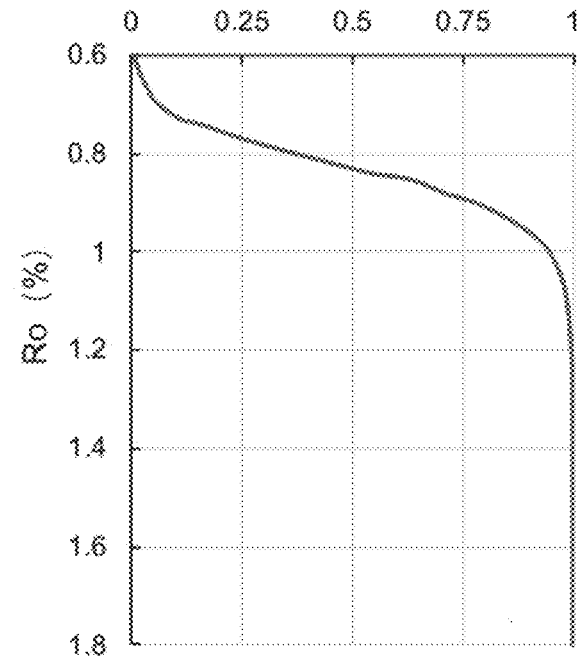
Figure 4C:
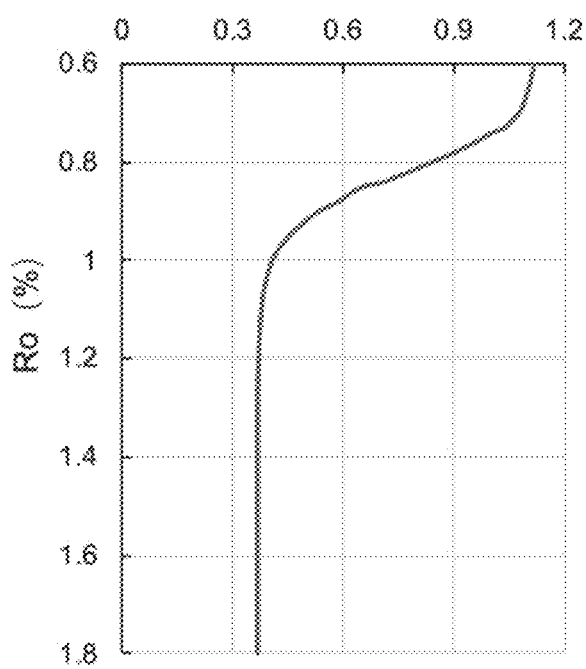
Figure 4D:
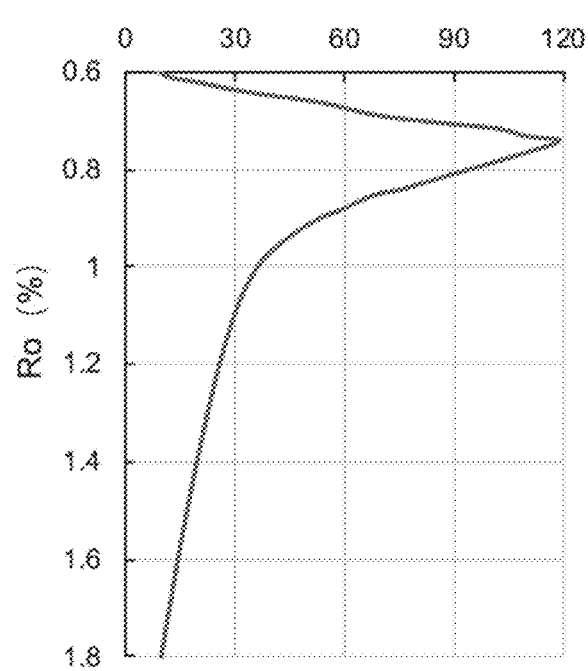

Taking the shale of the Qing-1 Member in the northern Songliao Basin as an example, the chemical kinetics parameters of primary cracking of kerogen are calibrated based on the pyrolysis gas chromatography (PY-GC) test results of an immature shale sample from the Qing-1 Member in the Du 402 well in the Taikang uplift in the northern Songliao Basin, as well as chemical kinetics principles. Based on the burial history and thermal history of the Songliao Basin, the transformation ratios (FIG. 4*b*) corresponding to different $R_o$ (vitrinite reflectance, VR) are calculated, and then the kerogen mass and amount (FIGS. 4*c* and 4*d*) of kerogen swelling oil in different evolution stages were calculated.

Step 102: Determine an amount of adsorbed oil on a wall of kerogen according to a cross-sectional area of the kerogen shale oil swelling and adsorption model and the kerogen and shale oil density curves, and calculate an amount of kerogen adsorbed oil per unit area according to the amount of adsorbed oil on the wall of kerogen and the cross-sectional area; determine a specific surface area of kerogen according to a number and diameter of organic pores in a shale sample; multiply the amount of kerogen adsorbed oil per unit area by the specific surface area of kerogen to obtain an amount of kerogen adsorbed oil.

The amount $Q_a$ of kerogen adsorbed oil per unit area is calculated by:

$$Q_a = (m_{a1} + m_{a2})/(2 \cdot S_{model})$$

Where $$m_{a1} = \int_{L1}^{L2} S_{model} \cdot \rho_{oil} dL$$

-continued $$m_{a2} = \int_{L3}^{L4} S_{model} \cdot \rho_{oil} dL$$

In the formula, $m_{a1}$ is an amount of adsorbed oil on a left side wall of kerogen; $L_1$ is a left side position of the intersection between the kerogen density curve and the shale oil density curve; $L_2$ is a left side position of a boundary between an adsorption zone and a free zone of the shale oil density curve; $M_{a2}$ is an amount of adsorbed oil on a right side wall of kerogen; $L_3$ is a right side position of the boundary between the adsorption zone and the free zone of the shale oil density curve; $L_4$ is a right side position of the intersection between the kerogen density curve and the shale oil density curve. The amount of adsorbed oil in type I kerogen per unit area is 1.149 mg/m².

The specific surface area of kerogen is specifically determined as follows:

divide shale pores into micropores (<10 nm), small pores (10-50 nm), medium pores (50-150 nm) and macropores (150-1,000 nm, 1,000-10,000 nm) according to logarithmic coordinates; equally divide each section of pore size into 10 parts; calculate surface areas of organic pores in an n-th section ($D_{n-1}$–$D_n$) of pore size; sum the specific surface areas of the n sections to obtain the surface area of the organic pores (the specific surface area of kerogen) SK:

$$SK = \sum_{1}^{n} SK_n$$

In the formula, n is a number of pore size sections of the shale, n=50, dimensionless; $SK_n$ is a specific surface area of a kerogen pore in the n-th section ($D_{n-1}$–$D_n$) of pore size, m².

Assuming that the organic pores in the n-th section ($D_{n-1}$–$D_n$) of pore size are composed of spherical pores with a diameter of $D_n$, then $SK_n$ is derived from the following formula:

$$SK_n = NK_n \cdot sK_{D_n} \cdot RK$$

In the formula, $NK_n$ is a number of organic pores in the n-th section ($D_{n-1}$–$D_n$) of pore size, dimensionless; $SK_{D_n}$ is a surface area of a single spherical pore with a diameter of $D_n$, m²; RK is a surface roughness coefficient of the kerogen pore, which is 1.2176 according to the surface roughness coefficient of kerogen pores in a Ha16 shale oil sample.

$SK_{D_n}$ is derived from a spherical surface area calculation formula:

$$sK_{D_n} = \pi D_n^2$$

The number $NK_n$ of organic pores in the n-th section ($D_{n-1}$–$D_n$) of pore size is obtained by dividing a volume $VK_n$ of the organic pores in the n-th section ($D_{n-1}$–$D_n$) of pore size by a volume $vK_{D_n}$ of a single spherical pore with a diameter of Da:

$$NK_{D_n} = \frac{VK_n}{vK_{D_n}} = \frac{V_\emptyset \cdot Pk_n}{\frac{4}{3}\pi\left(\frac{D_n}{2}\right)^3}$$

In the formula, $V_\emptyset$ is a kerogen pore volume corresponding to 1 g of original organic carbon, m³; $Pk_n$ is a proportion of the n-th section ($D_{n-1}$–$D_n$) of pore size to pore size distribution derived by a scanning electron microscope (SEM), dimensionless.

A proportion $Pk_n$ of the n-th section ($D_{n-1}$–$D_n$) of pore size to pore size distribution derived by nuclear magnetic resonance (NMR) is obtained by the following formula:

$$Pk_n = \frac{\int_0^{D_n} P_{SEM} dD - \int_0^{D_{n-k}} P_{SEM} dD}{\int_0^{D_n} P_{SEM} dD}$$

In the formula, $P_{SEM}$ is a proportion of pore size distribution derived by the SEM, dimensionless.

The volume of kerogen pores increases with the enhancement of hydrocarbon generation of kerogen, but due to swelling, some of the pores will be reduced. The compaction of the formation on the rock will also lead to the reduction of organic pores. Considering these factors, the organic pore volume $V_\emptyset$ corresponding to 1 g of original organic carbon is:

$$V_\emptyset = (V_{gh} - V_{sw}) \cdot V_{comp}$$

In the formula, $V_{gh}$ is an organic pore volume formed by kerogen generated oil and gas, cm³/g TOC; $V_{sw}$ is a kerogen swelled volume, cm³/IOC; $V_{os}$ is a volume of dead carbon generated by the cracking of oil into gas, cm³/g TOC; $V_{comp}$ is a compaction coefficient, dimensionless.

The organic pore volume $V_{gh}$ formed by kerogen generated oil and gas is derived from the following formula:

$$V_{gh} = V_f F_t$$

Figure 5A:
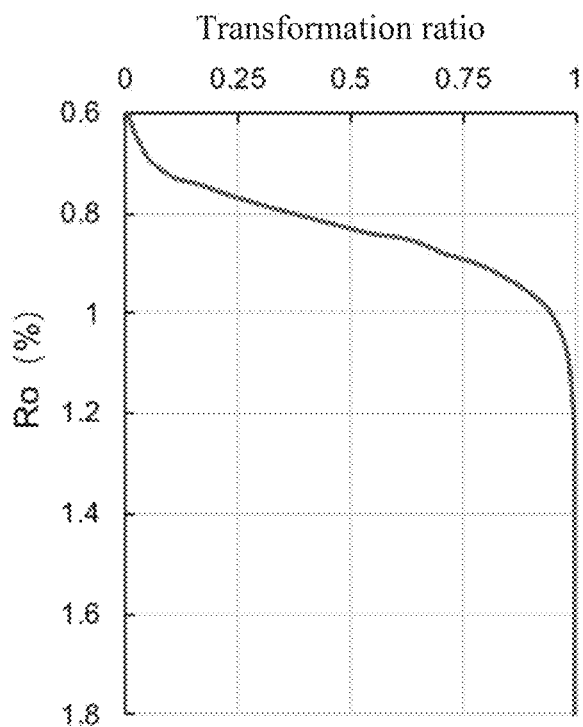
FIGS. 5(a) to 5(d) respectively show exemplary diagrams of a transformation ratio, a swelling ratio, an organic pore volume and a specific surface area of kerogen which evolve with $R_o$ in accordance with the present invention.

In the formula, $V_f$ is a volume of the transformable part of kerogen, cm³/g TOC; $F_t$ is a transformation ratio, dimensionless (FIG. 5a). The volume $V_t$ of the transformable part of kerogen is calculated from an original kerogen volume $V_k^0$ corresponding to 1 g of organic carbon and a volume $V_s$ of the non-transformable part of kerogen:

$$V_f = M_k^0 - V_s$$

$$V_k^0 = m_k^0 / \rho_k^0.$$

$$V_s = m_s / \rho_s$$

$$m_k^0 = HI^0 / 1000 + m_s$$

$$m_s = 1 - HI^0 \cdot 0.083/100$$

In the formula, $HI^0$ is an original hydrogen index, mg/g TOC (750 mg/g TOC); 0.083 is a carbon transformation coefficient of the hydrogen index, dimensionless; $m_k^0$ is a mass of immature kerogen; $\rho_k^0$ is a density of immature kerogen, g/cm³; $\rho_s$ is a density of the non-transformable part of kerogen, g/cm³. $\rho_k^0$ and $\rho_s$ are 1.25 g/cm³ and 1.35 g/cm³, respectively.

The organic pore volume $V_\emptyset$ is related to a kerogen swelling capacity $Q_v$ and the organic pore volume $V_{gh}$ formed by kerogen generated oil and gas:

$$V_\emptyset = \begin{cases} [V_f \cdot (1 - F_t) + V_s] \cdot Q_v & \text{if } [V_f \cdot (1 - F_t) + V_s] \cdot Q_v < V_{gh} l \\ V_{gh} & \text{if } [V_f \cdot (1 - F_t) + V_s] \cdot Q_v \geq V_{gh} l \end{cases}$$

Figure 5B:
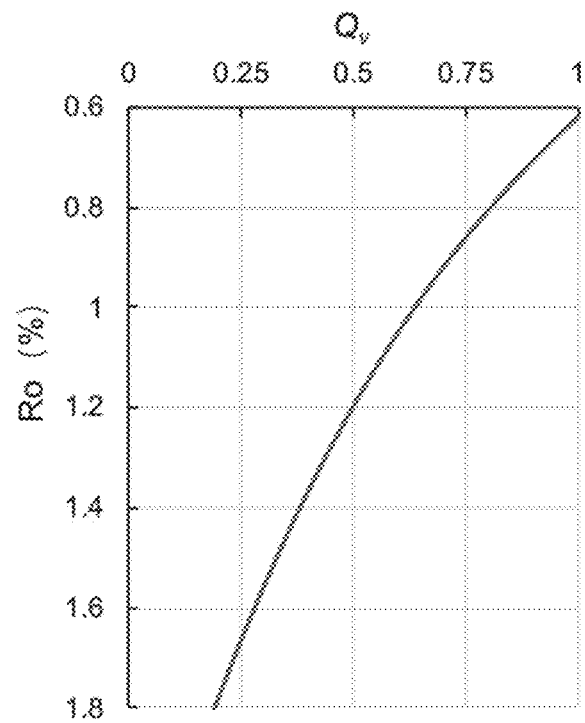

In the formula, $Q_v$ is a swelling ratio of type I kerogen, dimensionless, as shown in FIG. 5b.

Figure 5C:
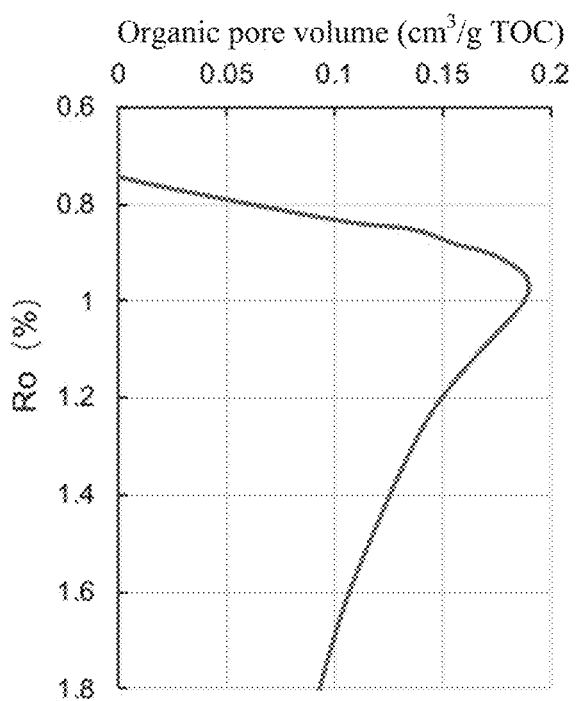
Figure 5D:
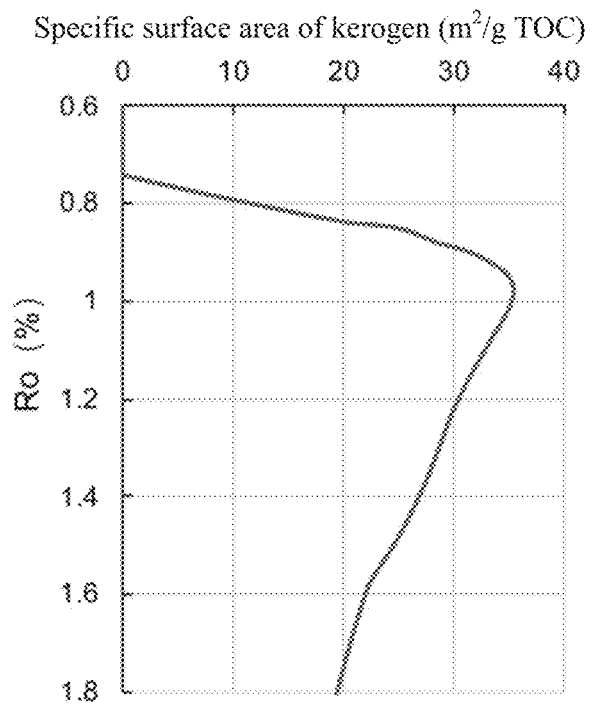

FIGS. 5c and 5d show evolutions of the organic pore volume and the specific surface area of kerogen with $R_o$. It can be seen from FIGS. 5a to 5d that with the increase of $R_o$ (VR, which reflects the change in the maturity of the organic matter), the organic pore volume and the specific surface area of kerogen both show a tendency of increasing first and then decreasing. However, due to the increase in the proportion of small pores and medium pores among the organic pores at the high evolution stage, the specific surface area of kerogen is less tended to decrease than the organic pore volume.

Step 103: Obtain a kerogen swelling capacity and an organic pore volume formed by kerogen generated oil and gas, and calculate an organic pore volume corresponding to organic carbon according to the kerogen swelling capacity and the organic pore volume formed by kerogen generated oil and gas; multiply a difference between the organic pore volume corresponding to the organic carbon and a volume of a kerogen adsorbed oil phase by a shale oil density, to obtain an amount of free oil in an organic pore.

Figure 6:
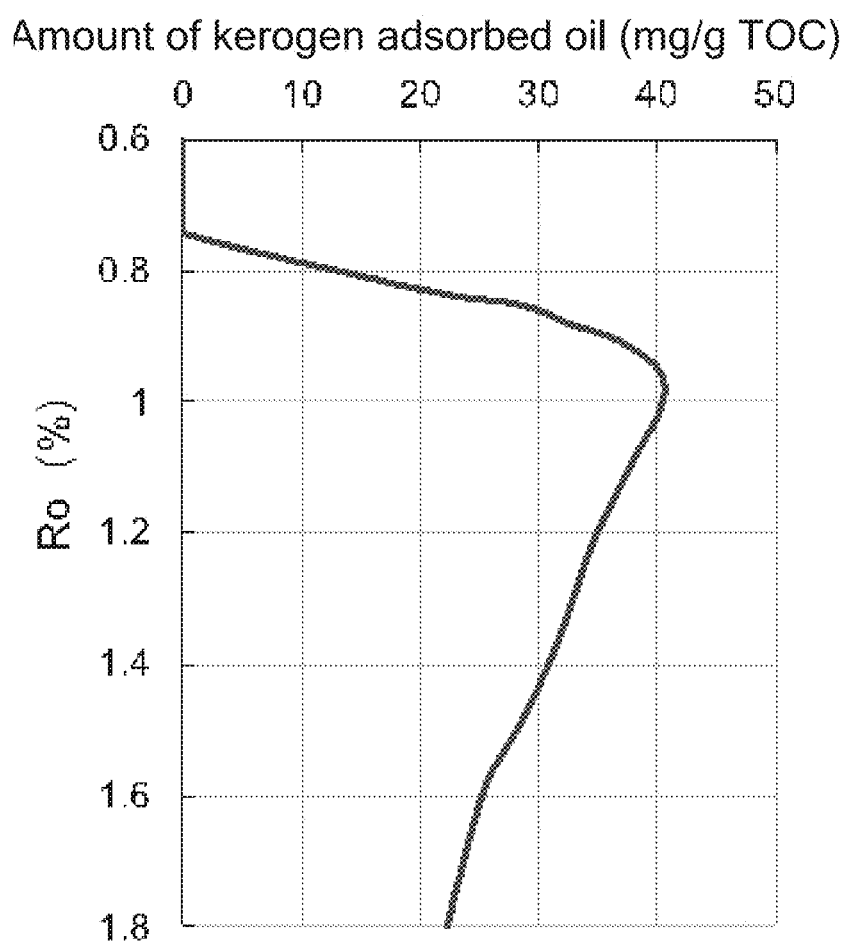
FIG. 6 shows an exemplary amount of kerogen adsorbed oil in accordance with the present invention.

The amount of kerogen adsorbed oil per unit area is multiplied by the specific surface area of kerogen to obtain the amount of kerogen adsorbed oil at different evolution stages (FIG. 6). The amount of kerogen adsorbed oil first increases and then decreases with the increase of $R_o$. Although the formation temperature increases with the increase of $R_o$, the change in the amount of adsorption per unit area due to temperature is small, and the amount of kerogen adsorbed oil has the same trend as the specific surface area of kerogen. The amount of kerogen absorbed oil is mainly controlled by the specific surface area of kerogen.

Shale oil mainly occurs in organic pores in adsorbed and free states. The free phase volume of shale oil is obtained by subtracting the adsorbed phase volume of shale oil from the volume of shale oil, and the free phase volume of shale oil is multiplied by the density of shale oil to obtain the amount $Q_{free}$ of free oil in the organic pore, as follows:

$$Q_{free}=(V_\varnothing-V_{ad})\cdot\rho_{oil}$$

In the formula, $V_{ad}$ is the volume of the kerogen adsorbed oil phase, $cm^3/g$ TOC, and $\rho_{oil}$ is the density of shale oil, $g/cm^3$.

$$V_{ad}=Q_{ad}/\rho_{ad}$$

In the formula, $Q_{ad}$ is an amount of kerogen adsorbed oil, mg/g TOC, and $\rho_{ad}$ is a density of kerogen adsorbed oil, $cm^3/g$ TOC.

Figure 7A:
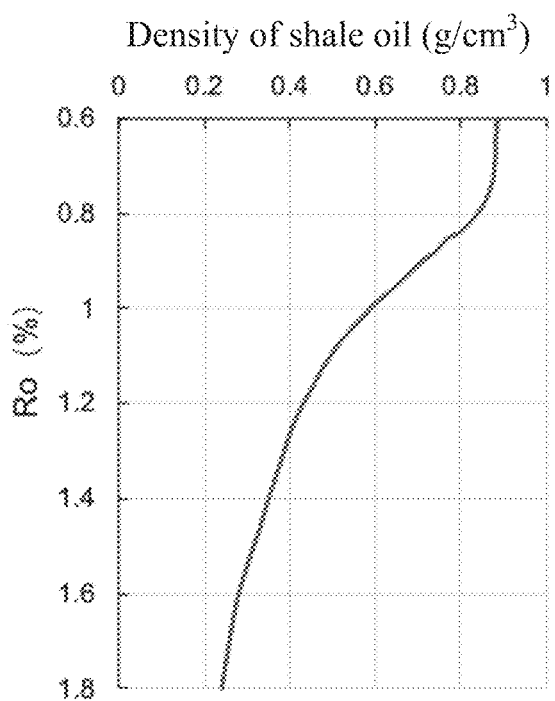
FIGS. 7(a) to 7(d) respectively show exemplary diagrams of a shale oil density, a volume of a kerogen adsorbed oil phase, a volume of a free oil phase in an organic pore and an amount of free oil in the organic pore which evolve with $R_o$ in accordance with the present invention.
Figure 7B:
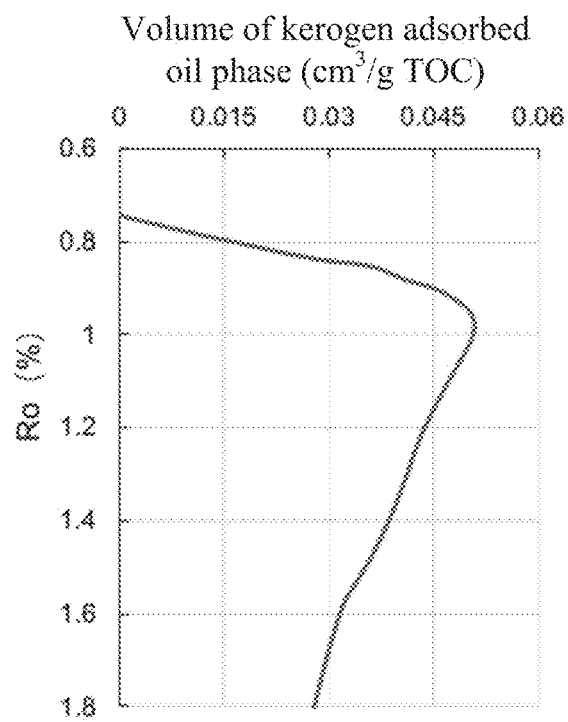
Figure 7C:
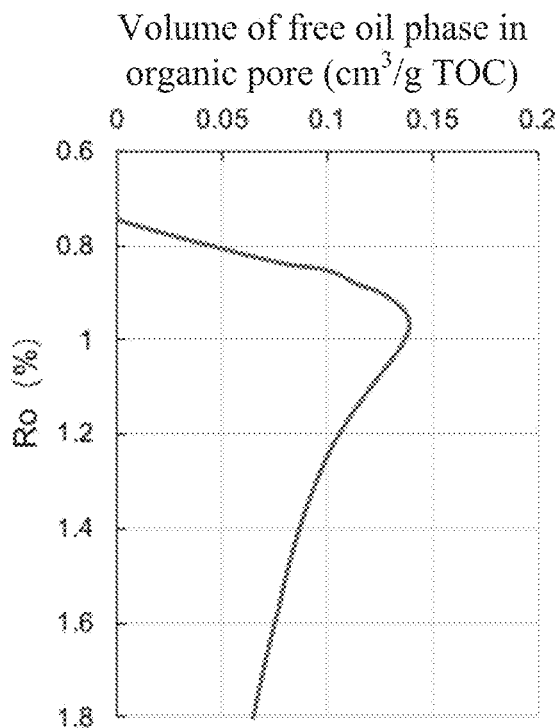
Figure 7D:
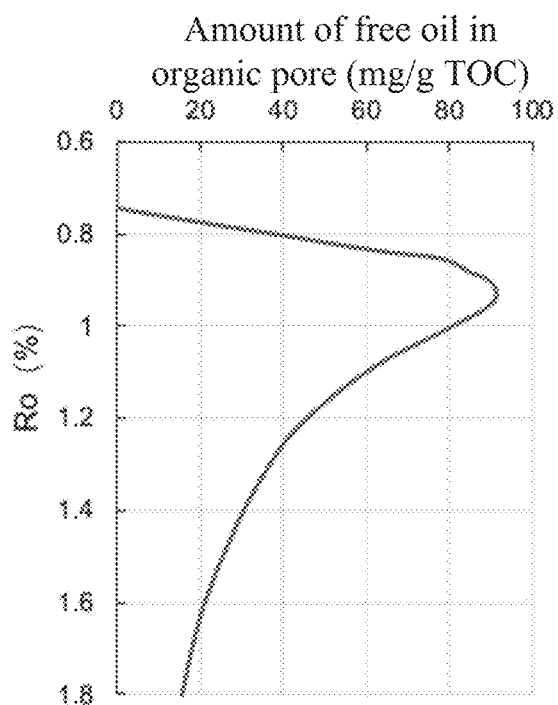

The kerogen adsorbed amount is divided by the density of the adsorbed phase of shale oil derived by molecular dynamics simulation to obtain the volume of the kerogen adsorbed oil phase (FIG. 7b). The organic pore volume is combined to obtain the volume of the free oil phase in the organic pore (FIG. 7c), and the free oil volume is multiplied by the density of shale oil (FIG. 7a), to finally obtain the trend of the amount of free oil in the organic pore evolving with $R_o$ (FIG. 7d). It can be seen from FIGS. 7a to 7d that the amount of free oil in the organic pore first increases and then decreases with the increase of $R_o$, and the maximum amount of free oil in the organic pore is 91.37 mg/g TOC, which is 2.24 times the maximum amount of kerogen absorbed oil, 40.82 mg/g TOC. Shale oil mainly occurs in the organic pores of type I kerogen in a free state.

Step 104: Divide the shale sample into a first shale sample and a second shale sample, and extract the first shale sample by using chloroform to obtain a total content of shale oil in the shale; sequentially enrich kerogen from the second shale sample, oven-dry, extract with chloroform and compare a mass of kerogen to obtain an amount of oil in an organic matter of the shale sample; determine an amount of oil in an inorganic mineral according to the total content of shale oil in the shale and the amount of oil in the organic matter of the shale sample.

The step specifically includes: obtain a shale sample and determine a parameter of the shale sample; divide the shale sample into a first shale sample and a second shale sample, and extract the first shale sample by using chloroform to obtain a total content of shale oil in the shale; enrich kerogen from the second shale sample to obtain dry kerogen; oven-dry the dry kerogen to obtain oven-dried kerogen, and determine a mass of the oven-dried kerogen; extract the oven-dried kerogen by using chloroform, and determine a mass of the extracted kerogen; determine a difference between the mass of the oven-dried kerogen and the mass of the extracted kerogen as an amount of oil in an organic matter; multiply a ratio of the amount of oil in the organic matter to a weight of the second shale sample by 100 to obtain an amount of oil in the organic matter of the shale sample; subtract the amount of oil in the organic matter of the shale sample from the total content of shale oil in the shale to obtain an amount of oil in an inorganic mineral of the shale sample; fit a ratio of the amount of oil in the inorganic mineral of the shale to the amount of oil in the organic matter of the shale sample and parameters of the shale sample to establish a model for predicting the ratio of the amount of oil in the inorganic mineral of the shale to the amount of oil in the organic matter; obtain an amount of oil in an organic matter of shale to be detected; and use the prediction model to determine an amount of oil in an inorganic mineral of the shale to be detected according to the amount of oil in the organic matter of the shale to be detected.

A representative shale sample (300-400 g) from a target area was crushed into 80-120 meshes, and divided into two samples. The mass of a first sample was measured ⅓ of the total mass, and recorded as $m_1$ (unit, g). An extraction test was performed on the first sample by using chloroform to obtain chloroform bitumen "A" in the shale, which was referred to as total "A" (unit, %) to represent a total content of shale oil in the shale, that is, a sum of the amount of oil in an inorganic mineral of the shale and the amount of oil in an organic matter of the shale. The mass of a second sample was measured ⅔ of the total mass, and recorded as $m_2$ (unit, g). The second shale sample was acid-treated to dissolve an inorganic mineral and enrich kerogen. It should be noted that in the last step of the standard kerogen enrichment experiment, the kerogen might not be extracted with chloroform. Instead, the enriched kerogen was first placed into an oven to dry at 110° C. for 6 h to remove moisture from the enriched kerogen. Then the oven-dried kerogen was taken out and weighed, and the mass of the dried kerogen was measured as $m_1$ (unit, g). The dried kerogen sample was then extracted with chloroform to obtain the amount of oil in the organic matter, which was recorded as $m_{a1}'$ (unit, g). By dividing $m_{a1}'$ by $m_2$ and multiplying by 100, the amount of oil in the organic matter of the shale was obtained, referred to as organic "A" (unit, %). Finally, by subtracting the organic "A" from the total "A", the amount of oil in the inorganic mineral of the shale was obtained, which was referred to as inorganic "A" (unit, %). The treatment results of 15 samples are shown in Table 1. In Table 1, Type represents the type of kerogen, $R_o$ represents VR, and TOC represents TOC in the sample.

TABLE 1

Geochemical data and calculated hydrocarbon content in the inorganic part of 15 samples

| Well No. | Depth (m) | Type | $R_o$ (%) | TOC (%) | Porosity (%) | Total "A" | Organic "A" (%) | Inorganic "A" (%) | Organic "A"/ Inorganic "A" (%) |
|---|---|---|---|---|---|---|---|---|---|
| Gu 204 | 2376 | II1 | 1.49 | 1.47 | 6.42 | 0.58 | 0.31 | 0.27 | 0.85 |
| Gu 844 | 2579 | II2 | 1.79 | 1.6 | 5.46 | 0.23 | 0.04 | 0.19 | 5.43 |
| Ying 39 | 2166 | II2 | 1.22 | 0.45 | 7.59 | 0.13 | 0.02 | 0.1 | 4.9 |
| Ying 52 | 2187.3 | II1 | 1.25 | 1.56 | 7.47 | 0.78 | 0.18 | 0.6 | 3.39 |
| Ying 52 | 2189 | II1 | 1.25 | 3.76 | 7.46 | 0.92 | 0.75 | 0.17 | 0.22 |
| Ying 52 | 2190.35 | II1 | 1.25 | 2.67 | 7.45 | 0.77 | 0.21 | 0.56 | 2.72 |
| Ying 52 | 2190.6 | II1 | 1.25 | 1.46 | 7.45 | 0.37 | 0.13 | 0.24 | 1.85 |
| Tai 602 | 1821 | I | 0.89 | 2.41 | 10.01 | 0.72 | 0.22 | 0.5 | 2.21 |
| Tai 602 | 1825.5 | I | 0.89 | 4.52 | 9.97 | 0.83 | 0.31 | 0.52 | 1.68 |
| Tai 602 | 1827 | I | 0.89 | 3.77 | 9.96 | 1.18 | 0.4 | 0.78 | 1.95 |
| Xu 11 | 1948 | I | 0.99 | 2.64 | 9.04 | 0.89 | 0.53 | 0.36 | 0.68 |
| Xu 11 | 1965.47 | I | 1.01 | 1.79 | 8.92 | 0.33 | 0.26 | 0.07 | 0.26 |
| Xu 11 | 1966.27 | I | 1.01 | 3.32 | 8.91 | 0.73 | 0.36 | 0.37 | 1 |
| Xu 11 | 1972 | I | 1.02 | 3.31 | 8.87 | 0.62 | 0.42 | 0.19 | 0.46 |
| Xu 11 | 1996.17 | I | 1.04 | 5.27 | 8.70 | 1.23 | 1.03 | 0.2 | 0.19 |

The representative shale sample from the target area was subjected to a whole-rock X-ray diffraction (XRD) test. The test results of the 15 samples are shown in Table 2.

TABLE 2

Inorganic mineral composition of 15 samples

| Well No. | Depth | Quartz | Clay mineral | Potash feldspar | Plagioclase | Calcite | Ferrodolomite | Dolomite | Siderite | Pyrite |
|---|---|---|---|---|---|---|---|---|---|---|
| Gu 204 | 2376 | 37.97 | 39.93 | | 12.23 | 1.43 | 6.96 | | 1.48 | |
| Gu 844 | 2579 | 37.06 | 36.93 | 0.45 | 14.71 | 3.36 | | | | 7.48 |
| Ying 391 | 2166 | 20.18 | 13.36 | | 35.65 | 24.82 | 4.84 | | | 1.15 |
| Ying 52 | 2187.3 | 41.44 | 36.01 | 2.41 | 19.21 | 0.93 | | | | |
| Ying 52 | 2189 | 36.11 | 41.21 | 0.72 | 13.49 | 1.55 | 6.92 | | | |
| Ying 52 | 2190.35 | 37.95 | 34.32 | | 16.61 | 4.57 | 1.71 | | 1.23 | 3.61 |
| Ying 52 | 2190.6 | 23.07 | 23.94 | | 7.67 | 5.35 | | | | 39.96 |
| Tai 602 | 1821 | 35.08 | 43.65 | | 14.92 | | | | | 6.35 |
| Tai 602 | 1825.5 | 33.88 | 41.06 | | 17.2 | | 1.12 | | 1.71 | 5.03 |
| Tai 602 | 1827 | 33.43 | 45.73 | | 16.97 | 3.86 | | | | |
| Xu 11 | 1948 | 33.25 | 38.73 | 1.12 | 13.56 | 4.09 | 4.45 | | | 4.81 |
| Xu 11 | 1965.47 | 32.65 | 38.58 | 1.81 | 20.13 | 0.81 | 0.44 | | 1.04 | 4.54 |
| Xu 11 | 1966.27 | 30.66 | 39.85 | | 14.87 | 9.06 | | | 1.8 | 3.77 |
| Xu 11 | 1972 | 11.51 | 12.24 | 2.17 | | 74.08 | | | | |
| Xu 11 | 1996.17 | 40.35 | 39.21 | 7.25 | 8.49 | | | 0.42 | 4.28 | |

The ratio of the inorganic "A" to the organic "A" ($W_{inorganic/organic}$), the quartz ratio, the clay mineral ratio, other mineral ratios, the TOC, the VR ($R_o$) and the porosity ($\Phi$) were fit by using matrix laboratory (MATLAB) to establish a $W_{inorganic/organic}$ prediction model. Undetermined parameters such as $M_{TOC}$, $M_q$, $M_c$, $M_o$, a, b, $d_1$ and $d_2$ in the prediction model were optimized based on experimental data, as shown in Table 3.

The prediction model is expressed by:

$$W_{inorganic/organic} = \frac{1}{\sqrt{2\pi} \cdot (d_1 + d_2)} (M_{TOC} \cdot TOC + M_q \cdot Quanrtz + M_c \cdot Clay + M_o \cdot Other) \cdot EXP\left[-\left(\frac{\ln R_o - a}{d_1}\right)^2 - \left(\frac{\ln \Phi - b}{d_2}\right)^2\right]$$

In the formula, $W_{inorganic/organic}$ indicates a ratio of the amount of oil in the inorganic mineral of the shale to the amount of oil in the organic matter of the shale sample; TOC indicates total organic carbon; $M_{TOC}$ indicates a TOC coefficient; Quartz indicates a quartz ratio; $M_q$ indicates a quartz ratio coefficient; Clay indicates a clay mineral ratio; $M_c$ indicates a clay ratio coefficient; Other indicates other ratio, such as a carbonate mineral ratio; $M_o$ indicates other mineral ratio coefficient, such as a carbonate mineral ratio coefficient; $R_o$ indicates a VR; a indicates a first VR coefficient; $d_1$ indicates a second VR coefficient; $\Phi$ indicates porosity; b indicates a first porosity coefficient; $d_2$ indicates a second porosity coefficient.

TABLE 3

Optimization results of parameters in the model

| Type | $M_{TOC}$ | $M_q$ | $M_C$ | $M_O$ | a | b | $d_1$ | $d_2$ |
|---|---|---|---|---|---|---|---|---|
| I | 3.93 | 1.67 | −2.86 | −0.75 | −0.27 | 2.41 | −9.20 | −0.18 |
| II | −0.60 | 0.76 | −0.72 | 0.00 | −0.75 | 2.89 | −1.12 | −1.12 |

Figure 8:
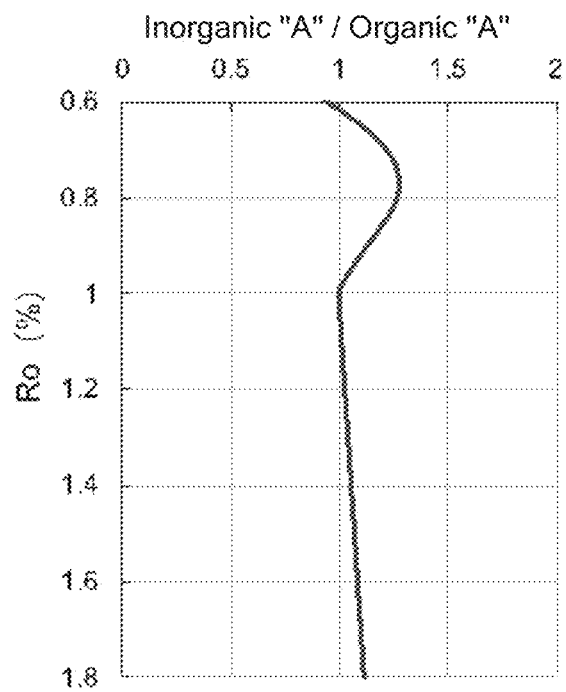
FIG. 8 shows an exemplary inorganic "A"/organic "A" ratio evolving with $R_o$ in accordance with the present invention.

Taking the inorganic mineral composition of the shale of deep lake to semi-deep lake facies in the Qing-1 Member of the Songliao Basin as an example, the average quartz ratio was 32.6%, the average clay mineral ratio as 37.2%, and the other average mineral ratio was 29.5%. Together with TOC=5%, these data were substituted into the $W_{inorganic/organic}$ prediction model to obtain the inorganic "A"/organic "A" ratio of the deep lake to semi-deep lake facies (FIG. 8). It can be seen from FIG. 8 that the inorganic "A"/organic "A" ratio tends to increase first and then decrease and then increase with the increase of $R_o$, and the maximum 1.281 is at a low maturity stage.

The amount of oil in the inorganic mineral of the shale to be detected is determined according to the following formula:

$$Q_{inorganic} = Q_{organic} \times W_{inorganic/organic}$$

In the formula, $Q_{inorganic}$ indicates the amount of oil in the inorganic mineral of the shale to be detected, and $Q_{inorganic}$ indicates the amount of oil in the organic matter of the shale to be detected.

Figures 9A, 9B:
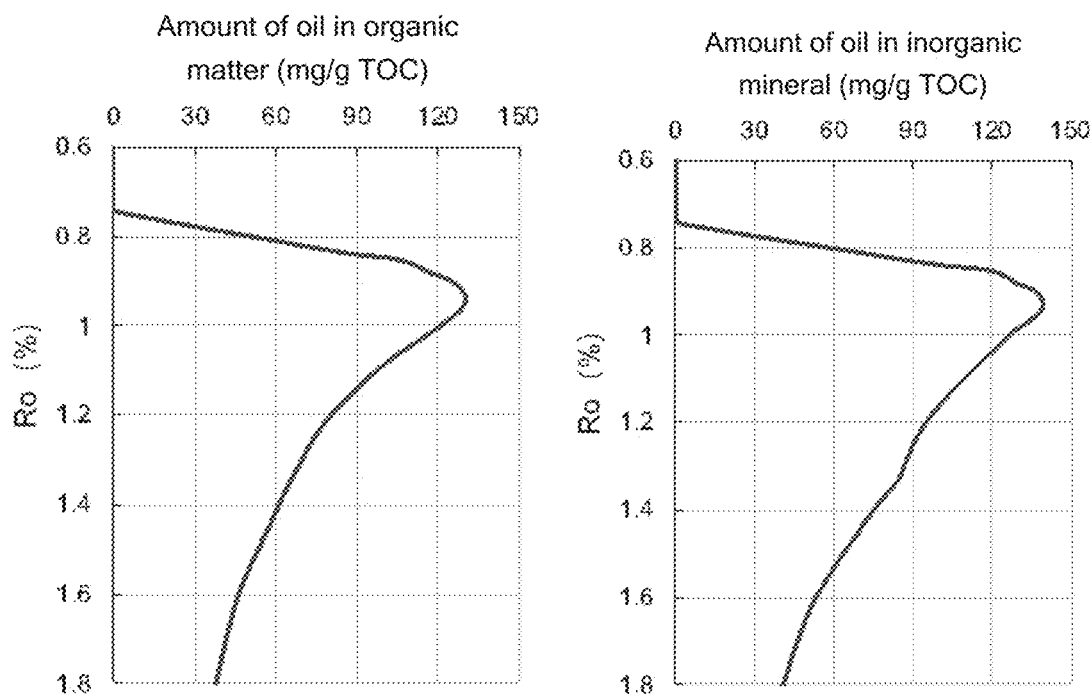
FIGS. 9(a) and 9(b) respectively show an exemplary amount of oil in an organic matter of shale and an exemplary amount of oil in an inorganic mineral of shale which evolve with $R_o$ in accordance with the present invention.

The amount of adsorbed oil by the organic matter and the amount of free oil in the organic matter are added together to obtain the amount of oil in the organic matter of the shale (FIG. 9a). The amount of oil in the organic matter of the shale is multiplied by the ratio of inorganic "A"/organic "A", that is, $W_{inorganic/organic}$, to obtain the amount of oil in the inorganic mineral of the shale (FIG. 9b). It can be seen from FIG. 9b that the amount of the shale oil in the inorganic part increases first and then decreases with $R_o$, with the maximum amount being 139.187 mg/g TOC.

Step 105: Load compound composition of shale oil into a kaolinite pore to obtain a kaolinite pore-shale oil model, and perform molecular dynamics simulation on the kaolinite pore-shale oil model to obtain a density curve of shale oil in the kaolinite pore; determine a surface oil adsorption capacity per unit area of kaolinite according to the density curve of shale oil in the kaolinite pore and a surface area of the kaolinite pore-shale oil model; determine a specific surface area of the inorganic mineral in the shale sample according to a number of inorganic pores in the shale sample and a surface area of an inorganic pore in the shale sample; multiply the surface oil adsorption capacity per unit area of kaolinite by the specific surface area of the inorganic mineral in the shale sample to obtain an amount of adsorbed oil by the inorganic mineral in the shale.

Figure 10A:
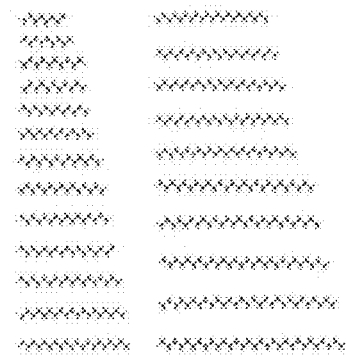
FIGS. 10(a) to 10(f) respectively show exemplary compound compositions of shale oil in accordance with the present invention.
Figure 10B:
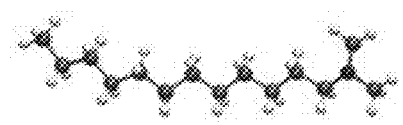
Figure 10C:
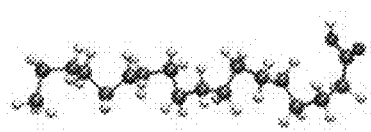
Figure 10D:
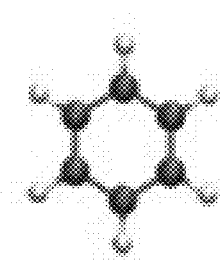
Figure 10E:
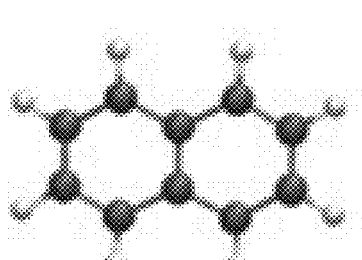
Figure 10F:
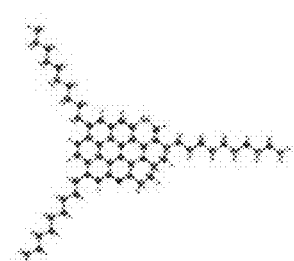
Figure 11:
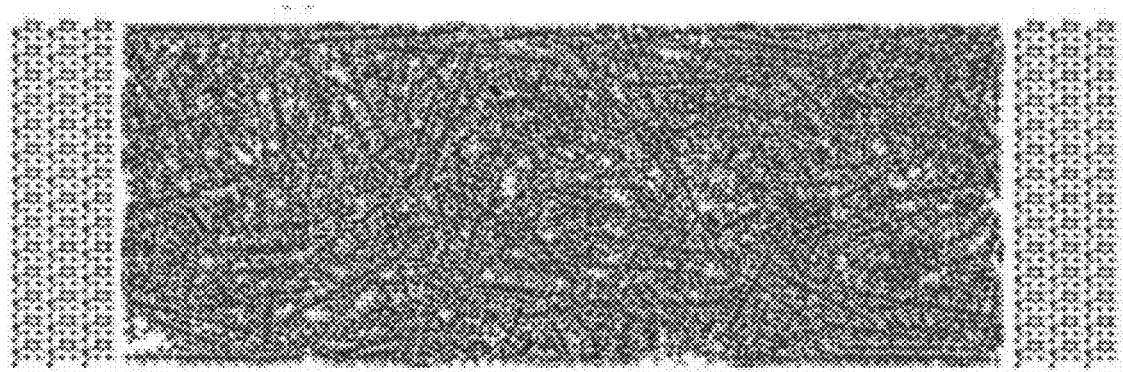
FIG. 11 shows an exemplary kaolinite pore-shale oil model in accordance with the present invention.

Based on the ratios of saturated hydrocarbons, aromatic hydrocarbons, non-hydrocarbon compounds, gums and asphaltenes which compose the shale oil family in the northern Songliao Basin and the GC of the saturated hydrocarbons, a shale oil molecular dynamics model close to the actual geological condition is established, as shown in FIGS. 10a to 10f. FIG. 10a shows $C_8H_{18}$ to $C_{30}H_{62}$, a total of 23 normal alkanes, which represent the saturated hydrocarbon components. FIGS. 10b and 10c show dimethyl dodecylamine ($C_{14}H_{31}N$) and n-octadecanoic acid ($C_{18}H_{36}O_2$) which represent the non-hydrocarbon compounds. FIGS. 10d and 10e show benzene ($C_6H_6$) and naphthalene ($C_{10}H_8$) which represent the aromatic hydrocarbon components. FIG. 10f shows asphaltene ($C_{60}H_{81}NS$) which represents the gum and asphaltene components. The lamellar kaolinite has unique physical properties. Its silicon-oxygen tetrahedron is a non-polar surface, while its aluminum-oxygen octahedron is a polar surface. The adsorption of shale oil in kaolinite indicates the adsorption characteristics of shale oil molecules on both polar and non-polar surfaces. Therefore, kaolinite is selected as the adsorbent to study the adsorption characteristics of shale oil on the surface of inorganic minerals. The PackMol software is used to load 28 compounds of shale oil into 13 nm wide kaolinite pores. FIG. 11 shows a kaolinite pore-shale oil model.

Figure 12A:
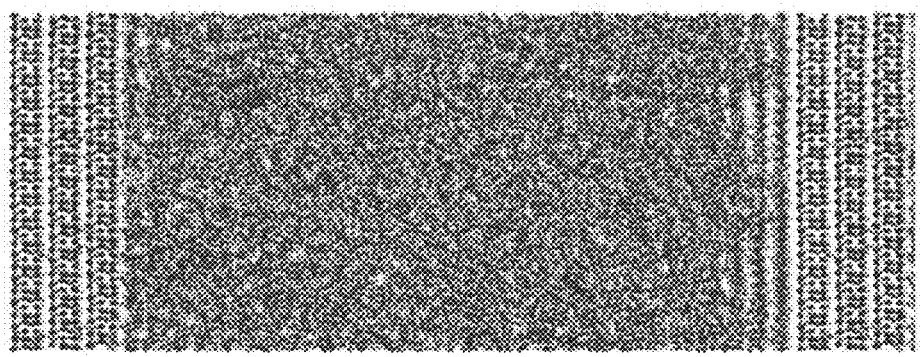
FIGS. 12(a) and 12(b) respectively show an exemplary last frame of adsorption simulation of shale oil in a kaolinite slit pore and a density curve of shale oil in the kaolinite pore in accordance with the present invention.
Figure 12B:
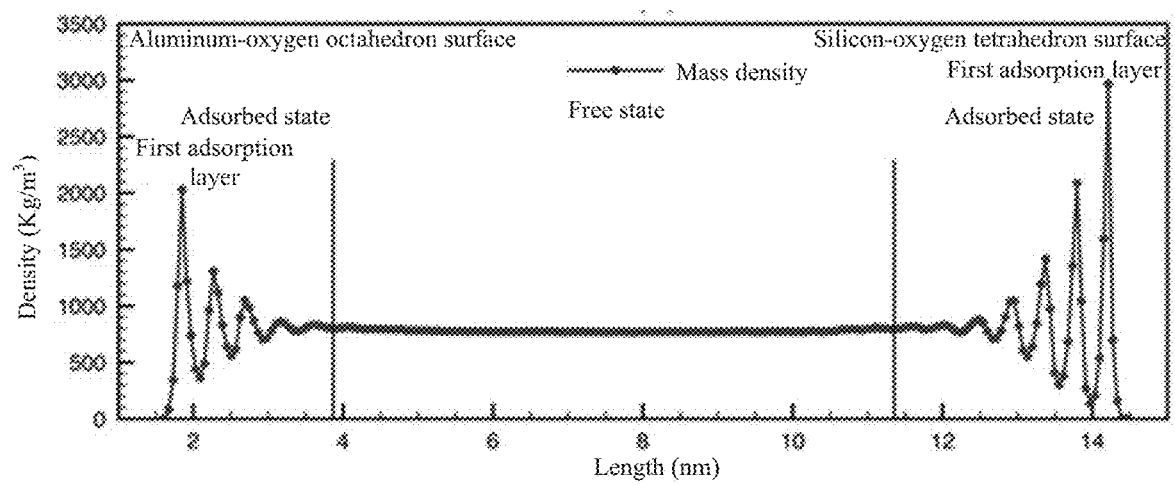

A ClayFF force field and a CHARMM 36/CGenFF force field are used to assign a value to force fields of kaolinite and shale oil molecules respectively, and an LB mixing rule is used to calculate an interaction force between the oil mixed molecules and clay minerals. A PME model is used as an electrostatic force model, and a van der Waals radius is 1.4 nm. The Gromacs software is first used to perform EM and relaxation on the kaolinite pore-shale oil model. Then, under the actual formation temperature and pressure conditions (348 K, 200 bar) in the northern Songliao Basin, molecular dynamics simulation is performed on the relaxed kaolinite pore-shale oil model for 200 ns by using the NPT ensemble. The last frame of the simulation of shale oil adsorption in the kaolinite slit pore is shown in FIG. 12a. The g_density module is used to process the simulation results to obtain a density curve of shale oil in the kaolinite pore, as shown in FIG. 12b. In FIG. 12b, the abscissa represents the length of the kaolinite pore and the ordinate represents the density.

The surface oil adsorption capacity per unit area of kaolinite is determined according to the following formula:

$$c = (c_{ada-a} + c_{ads-a})/2$$

$$c_{ada-a} = \frac{m_{ada}}{A_{ada}} = \frac{\int_{L_5}^{L_6} s_{model}^{(1)} \cdot \rho_{oil}^{(1)} dL}{A_{ada}}$$

$$c_{ads-a} = \frac{m_{ads}}{A_{ads}} = \frac{\int_{L_7}^{L_8} s_{model}^{(1)} \cdot \rho_{oil}^{(1)} dL}{A_{ads}}$$

In the formula, c represents the surface oil absorption capacity per unit area of kaolinite; $C_{ada-a}$ represents a surface oil absorption capacity per unit area of an aluminum-oxygen octahedron; $C_{ads-a}$ represents a surface oil absorption capacity per unit area of a silicon-oxygen tetrahedron; $m_{ada}$ represents a surface adsorption mass of the aluminum-oxygen octahedron; $m_{ads}$ represents a surface adsorption mass of the silicon-oxygen tetrahedron; $A_{ada}$ represents a surface area of the aluminum-oxygen octahedron in the kaolinite pore-shale oil model; $A_{ads}$ represents a surface area of the silicon-oxygen tetrahedron in the kaolinite pore-shale oil model; $s_{model}^{(1)}$ represents a cross-sectional area of the kaolinite pore-shale oil model; $\rho_{oil}^{(1)}$ represents a density curve of shale oil in the kaolinite pore; $L_5$ represents an initial position of the density curve of shale oil in the kaolinite pore; $L_6$ represents a cut-off position of a surface adsorption layer of the aluminum-oxygen octahedron; $L_7$ represents a position where an adsorbed phase separates from a free phase on a surface of the aluminum-oxygen octahedron; L represents a cut-off position of the density curve of shale oil in the kaolinite pore.

The specific surface area of the inorganic mineral in the shale sample is determined according to the following formula:

$$SM = \sum_1^n SM_n$$

Where $$SM_n = NM_{Dn} \cdot sM_{Dn}$$

$$sM_{Dn} = \pi D_n^2$$

$$NM_{Dn} = \frac{VM_n}{vM_{Dn}} = \frac{(V_{shale} \cdot \phi - TOC/100 \cdot V_\phi) \cdot P_n \cdot FM_n}{\frac{4}{3}\pi\left(\frac{D_n}{2}\right)^3}$$

$$P_n = \frac{\int_0^{D_n} P_{NMR} dD - \int_0^{D_{n1}} P_{NMR} dD}{\int_0^{D_n} P_{NMR} dD}$$

$$FM_n = \frac{Pm_n}{Pk_n + Pm_n}$$

$$Pk_n = \int_0^{D_n} Pk_{SEM} dD - \int_0^{D_{n-1}} Pk_{SEM} dD$$

$$Pm_n = \int_0^{D_n} Pm_{SEM} dD - \int_0^{D_{n-1}} Pm_{SEM} dD$$

In the formula, SM indicates the specific surface area of the inorganic mineral in the shale sample; n is a number of pore size sections of the shale sample; $SM_n$ is the specific surface area in the n-th section of pore size; $NM_{Dn}$ indicates a number of pores in the n-th section of pore size of 1 g of shale; $sM_{Dn}$ indicates a surface area of a single pore with a diameter of $D_n$; $VM_n$ indicates an inorganic pore volume of the shale sample in the n-th section of pore size; $vM_{Dn}$ indicates a volume of a single pore with a diameter of $D_n$; $V_{shale}$ indicates a volume of 1 g of shale sample; $\phi$ indicates the porosity of the shale sample; TOC indicates TOC; $V_\phi$ indicates an organic pore volume per unit mass of organic carbon; $P_n$ indicates a proportion of the n-th section of pore size to pore size distribution derived by NMR; $FM_n$ indicates a proportion of inorganic mineral pores of the shale sample in the n-th section of pore size; $D_n$ indicates a cut-off diameter of the n-th section of pore size; $D_{n-1}$ indicates an initial diameter of the n-th section of pore size; $P_{NMR}$ indicates a proportion of pore size distribution based on NMR; $Pk_n$ indicates a proportion of organic pore size in the n-th section to the pore size distribution derived by an SEM; $Pm_n$ indicates a proportion of inorganic pore size in the n-th section to the pore size distribution derived by the SEM; $Pk_{SEM}$ indicates organic pore size distribution derived by the SEM; $Pm_{SEM}$ indicates inorganic pore size distribution derived by the SEM.

Figure 13:
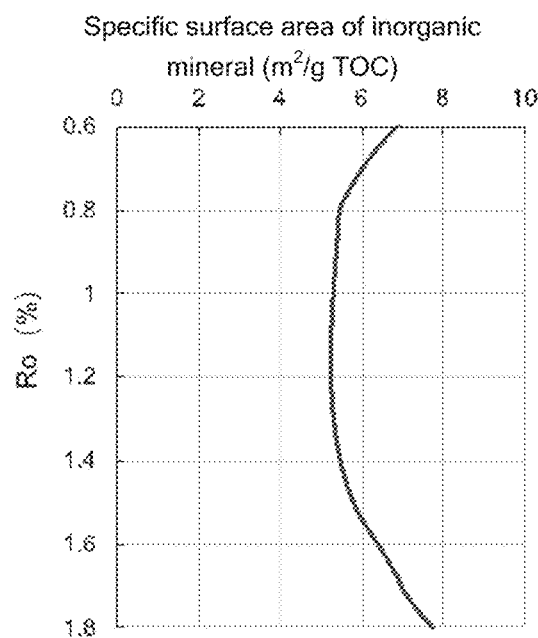
FIG. 13 shows an exemplary specific surface area of an inorganic mineral evolving with $R_o$ in accordance with the present invention.

After the specific surface area of inorganic mineral pores in 1 g of shale is obtained, it is used to normalize the TOC. The trend of the specific surface area of the inorganic minerals evolving with $R_o$ is derived through calculation (FIG. 13). It can be seen from FIG. 13 that the specific surface area of the inorganic minerals first decreases and then increases with the increase of $R_o$. When $R_o$ ranges from 0.6% to 1.2%, the proportion of macropores among the inorganic pores of shale increases, resulting in a continuous decrease in the specific surface area of the inorganic minerals. When $R_o$ is greater than 1.2%, the proportion of macropores in shale decreases and the proportion of small pores and medium pores increases, resulting in an increase in the specific surface area of the inorganic minerals.

Step 106: Determine a difference between the amount of oil in the inorganic mineral and the amount of adsorbed oil by the inorganic mineral in the shale as an amount of free oil in the inorganic pore.

Figure 14A:
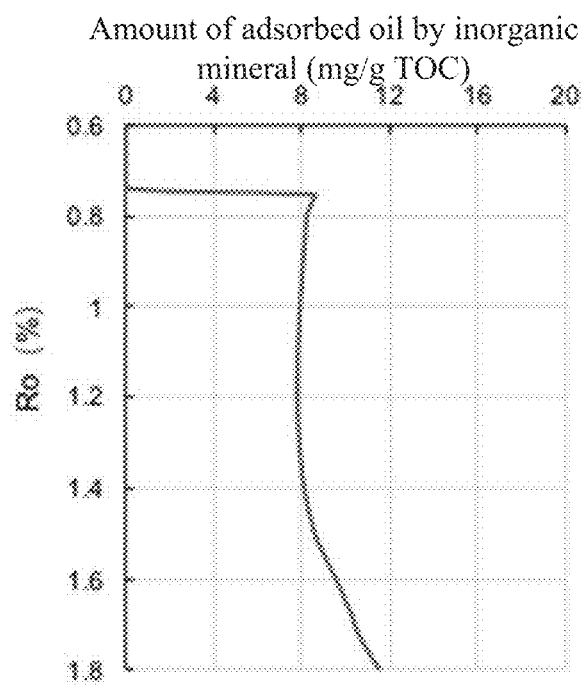
FIGS. 14(a) to 14(c) respectively show an exemplary amount of adsorbed oil by an inorganic mineral, an amount of oil in the inorganic mineral and an amount of free oil in an inorganic pore which evolve with $R_o$ in accordance with the present invention.
Figure 14B:
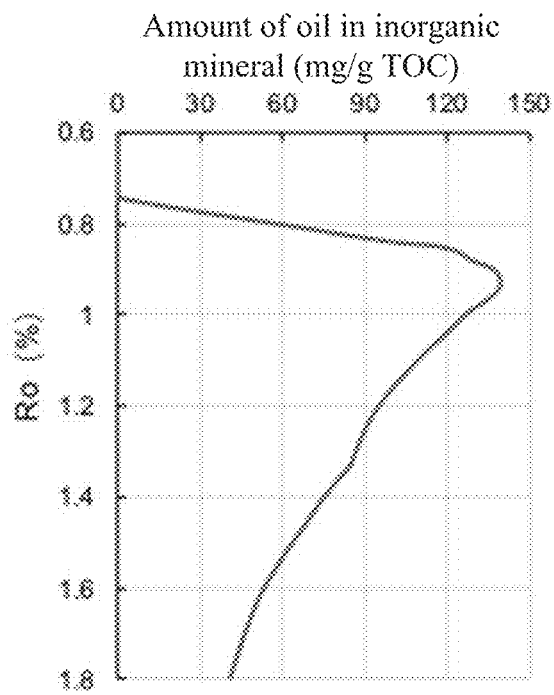
Figure 14C:
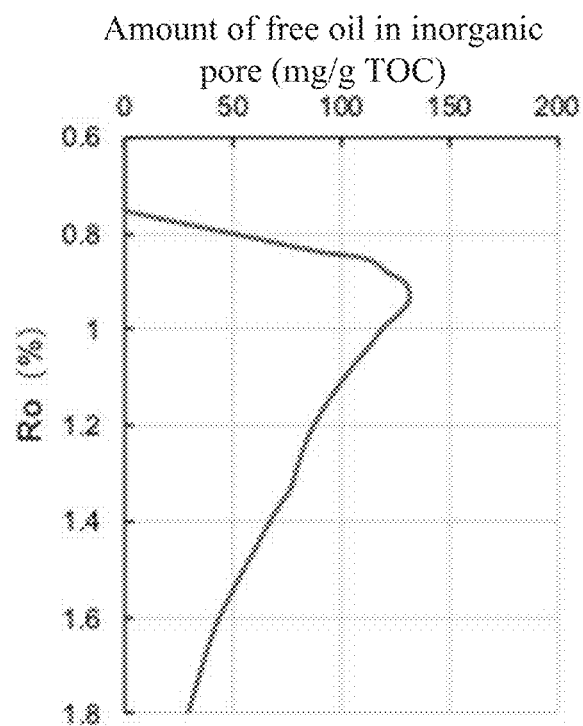

The amount of adsorbed oil per unit area of the inorganic mineral is multiplied by the specific surface area of the inorganic mineral to obtain the trend of the amount of adsorbed oil by the inorganic mineral evolving with $R_o$, as shown in FIG. 14a. The amount of adsorbed oil by the inorganic mineral is subtracted from the amount of oil in the inorganic mineral of the shale (FIG. 14b) to obtain the amount of free oil in the inorganic pore (FIG. 14c). The amount of adsorbed oil by the inorganic mineral tends to increase rapidly, then basically remain unchanged and finally increase slowly with the increase of $R_o$ (FIG. 14a). The shale oil first occurs in kerogen (swelling, adsorbed) and organic pores (free) and then enters inorganic pores. It is first adsorbed on the surface of inorganic minerals, which leads to a rapid increase in the amount of adsorbed oil by the inorganic minerals when $R_o$ ranges from 0.72% to 0.75%. When $R_o$ is greater than 0.75%, the evolution of the amount of adsorbed oil by the inorganic minerals is mainly controlled by the specific surface area of the inorganic minerals. The amount of free oil in the inorganic pores first increases and then decreases with the increase of $R_o$, with a maximum amount being 131.13 mg/g TOC (FIG. 14c). The amount of adsorbed oil by the inorganic minerals is much smaller than the amount of free oil in the inorganic pores. Shale oil is mainly in a free state in the inorganic pores, and the evolution trend of the free oil in the inorganic pores is mainly controlled by the amount of shale oil in the inorganic part.

Step 107: Establish an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detect an amount of shale oil according to the occurrence-state-based shale oil quantification model.

Figure 15:
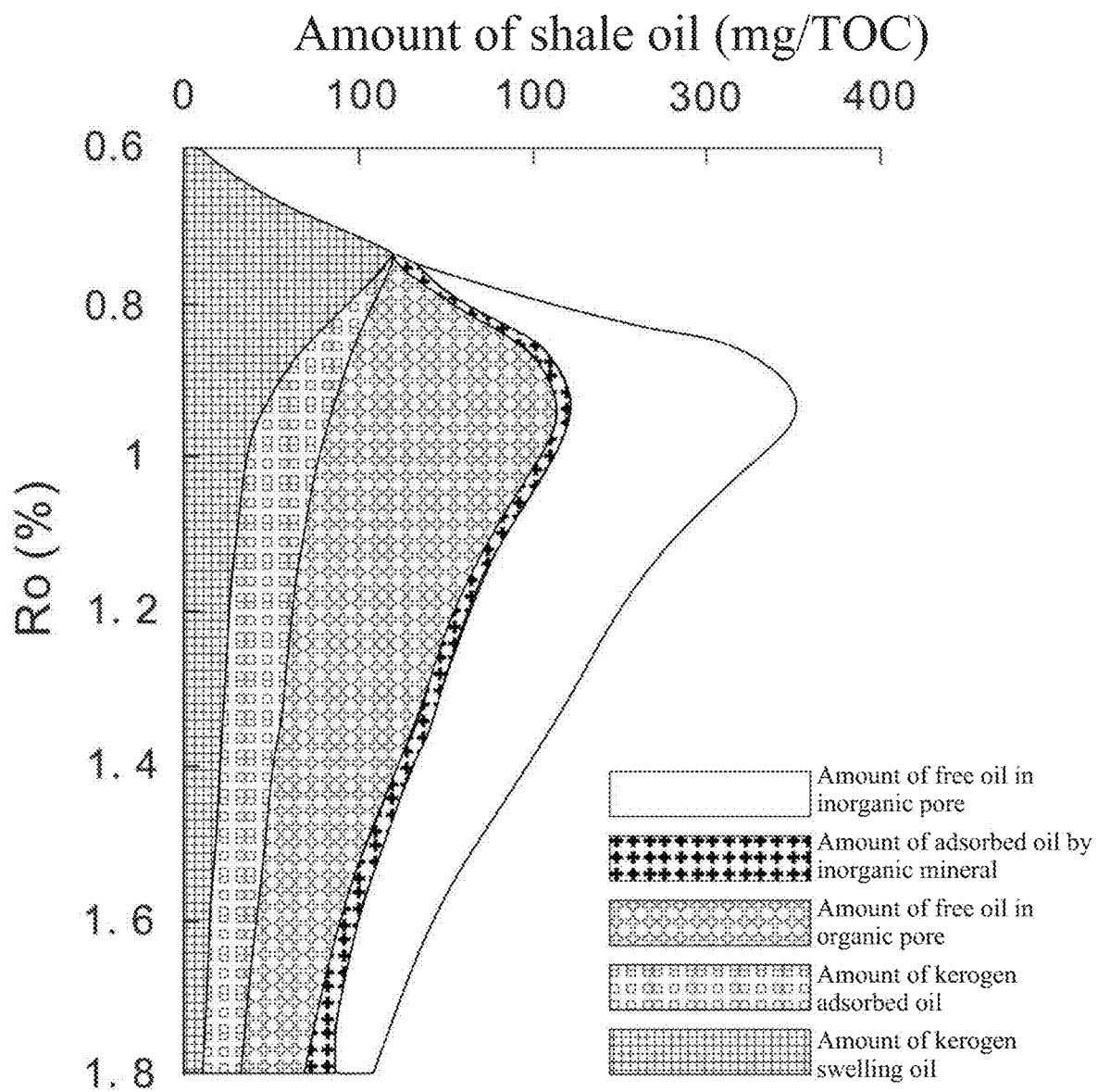
FIG. 15 shows an exemplary occurrence-state-based shale oil quantification model in accordance with the present invention.

The occurrence-state-based shale oil quantification model is shown in FIG. 15. It can be seen from FIG. 15 that as $R_o$ increases, the shale oil content in the shale tends to first increase and then decrease. When $R_o$ ranges from 0.6% to 0.8%, shale oil mainly occurs in the shale in a swelling state in kerogen. When $R_o$ ranges from 0.8% to 1.0%, as the kerogen generates a large amount of hydrocarbons, organic pores are formed rapidly. The shale oil generated from kerogen enters the organic pores after meeting the swelling and adsorption capacities of kerogen, and then enters the inorganic pores. At this stage, the amount of free oil in the organic pores and the amount of free oil in the inorganic pores increase rapidly. The swelling capacity of kerogen decreases with the deepening of evolution and the hydrocarbon generation of kerogen causes the mass to decrease, which leads to a continuous decrease in the amount of kerogen swelling oil. When $R_o$ is greater than 1.0%, the amount of kerogen swelling oil, the amount of kerogen adsorbed oil, the amount of free oil in the organic pores and the amount of free oil in the inorganic pores all decrease with the increase of $R_o$. However, the shale oil mainly exists as free oil in the organic pores and inorganic pores.

Step 101 of the present invention uses a real kerogen model to overcome the problems caused by the conventional method of using simple graphene to study the adsorption of shale oil by kerogen. Graphene is a two-dimensional carbon material, which has a smooth surface and a surface structure different from kerogen molecules. The shale oil molecules cannot pass through the graphene to enter its lamellar structure, and cannot make the graphene swell like a real kerogen structure. The kerogen aggregate model is preprocessed to prevent incomplete compaction of the kerogen aggregate. If the kerogen aggregate is incompletely compacted, it will lead to large pores inside, making the density of the kerogen aggregate model lower than that of the kerogen sample.

Step 102 of the present invention processes the amount of kerogen swelling oil per unit mass and the amount of kerogen adsorbed oil per unit area, which overcomes the problem that the conventionally used molecular dynamics simulation system is too small to be applied to the adsorption of shale oil. The shale oil-kerogen system used for molecular dynamics simulation is usually less than 20 nm while the pore size of a shale reservoir is dominantly greater than 20 nm. The present invention calculates the amount of kerogen swelling oil per unit mass, and calculates the kerogen swelling ratio based on the actual geological parameter i.e. swelling coefficient reduction. The present invention then calculates the amount of kerogen adsorbed oil per unit area, and calculates the amount of kerogen adsorbed oil based on the actual geological parameter i.e. the specific surface area of kerogen. In this way, the present invention greatly improves the accuracy of the results.

Step 103 quantitatively evaluates the amount of free oil in the kerogen at different evolution stages, which provides important parameters for shale oil mobility evaluation, and improves the accuracy of shale oil mobility evaluation.

Step 104 extracts the shale sample and the enriched kerogen sample separately, which solves the problem that the chloroform bitumen "A" could not distinguish between oil in the inorganic minerals of shale and oil in the organic matter of shale in the past. Meanwhile, the quantitative evaluation on the amount of oil in the inorganic minerals of shale at different evolution stages provides important parameters for shale oil mobility evaluation, and improves the accuracy of shale oil mobility evaluation.

Step 105 performs the molecular dynamics simulation of shale oil based on the shale oil components of a geological sample, which overcomes the problem of conventionally using a single component to replace the shale oil model, and improves the accuracy of the molecular dynamics simulation results.

Step 106 of the present invention processes the amount of adsorbed oil by the inorganic minerals per unit area, which overcomes the problem that the conventionally used molecular dynamics simulation system is too small to be applied to the adsorption of shale oil. The shale oil-inorganic mineral system used for molecular dynamics simulation is usually less than 20 nm, while the pore size of a shale reservoir is dominantly greater than 20 nm. The present invention calculates the amount of kerogen adsorbed oil per unit area, and calculates the amount of adsorbed oil by the inorganic minerals based on the actual geological parameter i.e. the specific surface area of the inorganic minerals. The present invention greatly improves the accuracy of the results. In addition, the quantitative evaluation on the amount of adsorbed and free oil among the amount of oil in the inorganic minerals of shale at different evolution stages provides important parameters for shale oil mobility evaluation, and improves the accuracy of shale oil mobility evaluation.

Figure 16:
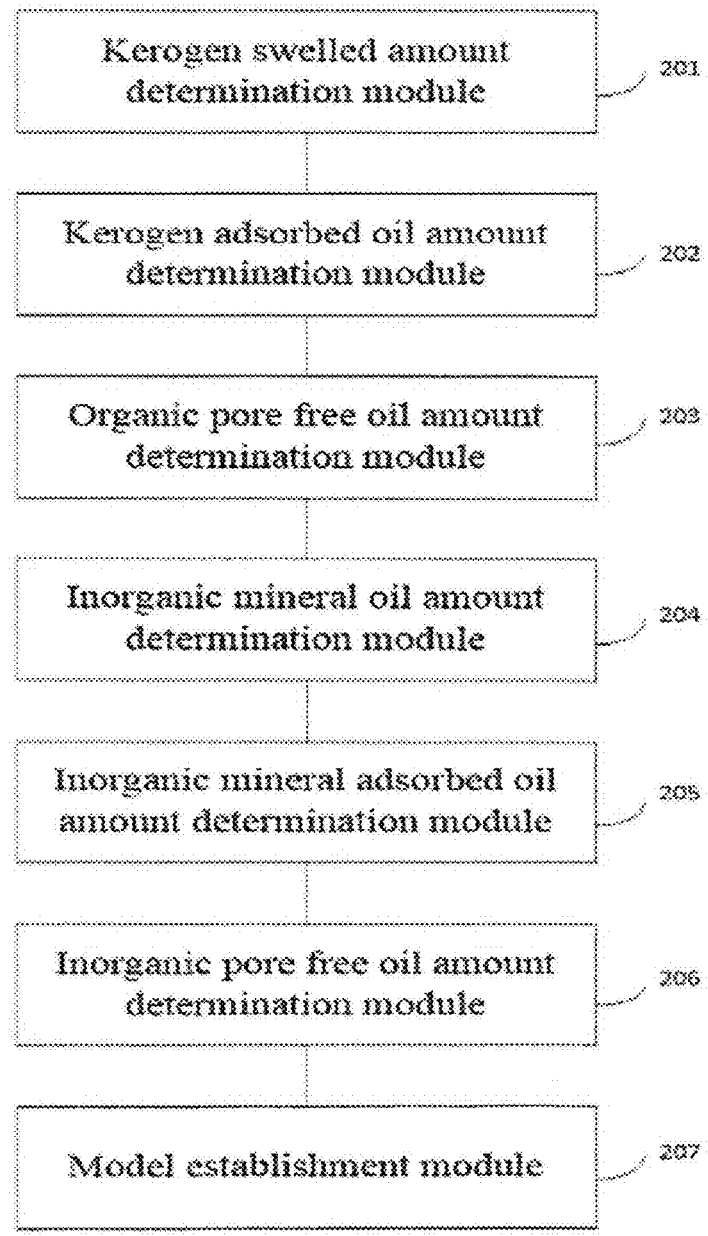
FIG. 16 is a structural diagram of a system for detecting an amount of shale oil based on an occurrence state in accordance with the present invention.

FIG. 16 is a structural diagram of a system for detecting an amount of shale oil based on an occurrence state according to an example of the present invention. As shown in FIG. 16, the system for detecting an amount of shale oil based on an occurrence state, along with a processor and memory, includes: a kerogen swelled amount determination module 201, a kerogen adsorbed oil amount determination module 202, an organic pore free oil amount determination module 203, an inorganic mineral oil amount determination module 204, an inorganic mineral adsorbed oil amount determination module 205, an inorganic pore free oil amount determination module 206 and a model establishment module 207.

The kerogen swelled amount determination module 201 is used for obtaining a kerogen molecular model, loading the kerogen molecular model into a pore formed by a graphene lamellar structure, and performing EM, relaxation, simulated annealing and shale oil molecular loading in sequence to obtain a swelling and adsorption model of shale oil in kerogen; assigning a value to force fields of a shale oil molecule and a kerogen molecule in the kerogen shale oil swelling and adsorption model to determine kerogen and shale oil density curves; calculating a kerogen swelled amount according to the kerogen and shale oil density curves.

The kerogen adsorbed oil amount determination module 202 is used for determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area; determining a specific surface area of kerogen according to a number and diameter of organic pores in a shale sample; multiplying the amount of kerogen adsorbed oil per unit area by the specific surface area of kerogen to obtain an amount of kerogen adsorbed oil.

The organic pore free oil amount determination module 203 is used for obtaining a kerogen swelling capacity and an organic pore volume formed by kerogen generated oil and gas, and calculating an organic pore volume corresponding to organic carbon according to the kerogen swelling capacity and the organic pore volume formed by kerogen generated oil and gas; multiplying a difference between the organic pore volume corresponding to the organic carbon and a volume of a kerogen adsorbed oil phase by a shale oil density, to obtain an amount of free oil in an organic pore, where the volume of the kerogen adsorbed oil phase is a ratio of the amount of kerogen adsorbed oil to a density thereof.

The inorganic mineral oil amount determination module 204 is used for dividing the shale sample into a first shale sample and a second shale sample, and extracting the first shale sample by using chloroform to obtain a total content of shale oil in the shale; sequentially enriching kerogen from the second shale sample, oven-drying, extracting with chloroform and comparing a mass of kerogen to obtain an amount of oil in an organic matter of the shale sample; determining an amount of oil in an inorganic mineral according to the total content of shale oil in the shale and the amount of oil in the organic matter of the shale sample.

The inorganic mineral adsorbed oil amount determination module 205 is used for loading compound composition of shale oil into a kaolinite pore to obtain a kaolinite pore-shale oil model, and performing molecular dynamics simulation on the kaolinite pore-shale oil model to obtain a density curve of shale oil in the kaolinite pore; determining a surface oil adsorption capacity per unit area of kaolinite according to the density curve of shale oil in the kaolinite pore and a surface area of the kaolinite pore-shale oil model; determining a specific surface area of the inorganic mineral in the shale sample according to a number of inorganic pores in the shale sample and a surface area of an inorganic pore in the shale sample; multiplying the surface oil adsorption capacity per unit area of kaolinite by the specific surface area of the inorganic mineral in the shale sample to obtain an amount of adsorbed oil by the inorganic mineral in the shale.

The inorganic pore free oil amount determination module 206 is used for determining a difference between amount of oil in the inorganic mineral and the amount of adsorbed oil by the inorganic mineral in the shale as an amount of free oil in the inorganic pore.

The model establishment module 207 is used for establishing an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detecting an amount of shale oil according to the occurrence-state-based shale oil quantification model.

For a system disclosed in the examples, since it corresponds to the method disclosed in the examples, the description is relatively simple, and reference can be made to the method description.

Several examples are used for illustration of the principles and implementation methods of the present invention. The description of the examples is used to help illustrate the method and its core principles of the present invention. In addition, those skilled in the art can make various modifications in terms of specific examples and scope of application in accordance with the teachings of the present invention. In conclusion, the content of this specification shall not be construed as a limitation to the present invention.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for detecting an amount of shale oil based on an occurrence state, comprising:

obtaining a kerogen molecular model, loading the kerogen molecular model into a pore formed by a graphene lamellar structure, and performing energy minimization (EM), relaxation, simulated annealing and shale oil molecular loading in sequence to obtain a swelling and adsorption model of shale oil in kerogen; assigning a value to force fields of a shale oil molecule and a kerogen molecule in the kerogen shale oil swelling and adsorption model to determine kerogen and shale oil density curves; calculating a kerogen swelled amount according to the kerogen and shale oil density curves;

determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area; determining a specific surface area of kerogen according to a number and diameter of organic pores in a shale sample; multiplying the amount of kerogen adsorbed oil per unit area by the specific surface area of kerogen to obtain an amount of kerogen adsorbed oil;

obtaining a kerogen swelling capacity and an organic pore volume formed by kerogen generated oil and gas, and calculating an organic pore volume corresponding to organic carbon according to the kerogen swelling capacity and the organic pore volume formed by kerogen generated oil and gas; multiplying a difference between the organic pore volume corresponding to the organic carbon and a volume of a kerogen adsorbed oil phase by a shale oil density, to obtain an amount of free oil in an organic pore, wherein the volume of the kerogen adsorbed oil phase is a ratio of the amount of kerogen adsorbed oil to a density thereof;

dividing the shale sample into a first shale sample and a second shale sample, and extracting the first shale sample by using chloroform to obtain a total content of shale oil in the shale; sequentially enriching kerogen from the second shale sample, oven-drying, extracting with chloroform and comparing a mass of kerogen to obtain an amount of oil in an organic matter of the shale sample; determining an amount of oil in an inorganic mineral according to the total content of shale oil in the shale and the amount of oil in the organic matter of the shale sample;

loading compound composition of shale oil into a kaolinite pore to obtain a kaolinite pore-shale oil model, and performing molecular dynamics simulation on the kaolinite pore-shale oil model to obtain a density curve of shale oil in the kaolinite pore; determining a surface oil adsorption capacity per unit area of kaolinite according to the density curve of shale oil in the kaolinite pore and a surface area of the kaolinite pore-shale oil model; determining a specific surface area of the inorganic mineral in the shale sample according to a number of inorganic pores in the shale sample and a surface area of an inorganic pore in the shale sample; multiplying the surface oil adsorption capacity per unit area of kaolinite by the specific surface area of the inorganic mineral in the shale sample to obtain an amount of adsorbed oil by the inorganic mineral in the shale;

determining a difference between the amount of oil in the inorganic mineral and the amount of adsorbed oil by the inorganic mineral in the shale as an amount of free oil in the inorganic pore; and establishing an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detecting an amount of shale oil according to the occurrence-state-based shale oil quantification model;

wherein said obtaining a kerogen molecular model, loading the kerogen molecular model into a pore formed by a graphene lamellar structure, and performing EM, relaxation, simulated annealing and shale oil molecular loading in sequence to obtain a swelling and adsorption model of shale oil in kerogen comprises:

loading the kerogen molecular model into a pore formed by a graphene lamellar structure, then performing EM, and performing relaxation at 75° C. under 20 MPa for 200 ps to obtain a compacted kerogen aggregate model;

subjecting the compacted kerogen aggregate model to 200 ps relaxation warming, and performing simulation by using a constant number of particles, pressure, and temperature (NPT) ensemble at 800° C. under normal pressure for 2 ns to obtain a kerogen slit pore; and loading a shale oil molecule into the kerogen slit pore to obtain a swelling and adsorption model of shale oil in kerogen.

2. The method for detecting an amount of shale oil based on an occurrence state according to claim 1, wherein said calculating a kerogen swelled amount according to the kerogen and shale oil density curves specifically comprises:

calculating an amount of kerogen swelling oil by $$Q_{oil} = \int_{L_{o1}}^{L_{o2}} S_{model} \cdot \rho_{oil} dL$$

according to the kerogen and shale oil density curves, wherein, $Q_{oil}$ is the amount of kerogen swelling oil; $L_{o1}$ is an initial position of an intersection between the kerogen density curve and the shale oil density curve; $L_{o2}$ is a cut-off position of the intersection between the kerogen density curve and the shale oil density curve; $S_{model}$ is a cross-sectional area of the kerogen shale oil swelling and adsorption model; $\rho_{oil}$ is the shale oil density curve;

obtaining a mass of kerogen, and dividing the amount of kerogen swelling oil by the mass of kerogen to obtain an amount of kerogen swelling oil per unit mass; and calculating a kerogen swelled amount $Q_s$ by $Q_s = Q_w \cdot m_k \cdot f_s$ according to the amount of kerogen swelling oil per unit mass, wherein $Q_w$ is the amount of kerogen swelling oil per unit mass; $m_k$ is a kerogen mass corresponding to 1 g of organic carbon; $f_s$ is a swelling ratio reduction coefficient.

3. The method for detecting an amount of shale oil based on an occurrence state according to claim 2, wherein said determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area specifically comprises:

calculating an amount $Q_a$ of kerogen adsorbed oil per unit area by:

$$Q_a = (m_{a1} + m_{a2})/(2 \cdot S_{model})$$

wherein $$m_{a1} = \int_{L1}^{L2} S_{model} \cdot \rho_{oil} dL$$

$$m_{a2} = \int_{L3}^{L4} S_{model} \cdot \rho_{oil} dL$$

wherein, $m_{a1}$ is an amount of adsorbed oil on a left side wall of kerogen; $L_1$ is a left side position of the intersection between the kerogen density curve and the shale oil density curve; $L_2$ is a left side position of a boundary between an adsorption zone and a free zone of the shale oil density curve; $M_{a2}$ is an amount of adsorbed oil on a right side wall of kerogen; $L_3$ is a right side position of the boundary between the adsorption zone and the free zone of the shale oil density curve; $L_4$ is a right side position of the intersection between the kerogen density curve and the shale oil density curve.

4. The method for detecting an amount of shale oil based on an occurrence state according to claim 3, wherein said calculating an organic pore volume corresponding to organic carbon according to the kerogen swelling capacity and the organic pore volume formed by kerogen generated oil and gas specifically comprises:

calculating an organic pore volume corresponding to organic carbon by:

$$V_\emptyset = \begin{cases} [V_f \cdot (1 - F_t) + V_s] \cdot Q_v & \text{if } [V_f \cdot (1 - F_t) + V_s] \cdot Q_v < V_{gh}l \\ V_{gh} & \text{if } [V_f \cdot (1 - F_t) + V_s] \cdot Q_v \geq V_{gh}l \end{cases}$$

wherein, $V_\emptyset$ is the organic pore volume corresponding to organic carbon, $V_f$ is a volume of a transformable part of kerogen, $F_t$ is a transformation ratio, $V_s$ is a volume of a non-transformable part of kerogen, $Q_v$ is the kerogen swelling capacity, and $V_{gh}$ is the organic pore volume formed by kerogen generated oil and gas.

5. The method for detecting an amount of shale oil based on an occurrence state according to claim 4, wherein said sequentially enriching kerogen from the second shale sample, oven-drying, extracting with chloroform and comparing a mass of kerogen, to obtain an amount of oil in the organic matter of the shale sample specifically comprises:
  enriching kerogen from the second shale sample to obtain dry kerogen;
  oven-drying the dry kerogen to obtain oven-dried kerogen, and determining a mass of the oven-dried kerogen;
  extracting the oven-dried kerogen by using chloroform, and determining a mass of the extracted kerogen;
  determining a difference between the mass of the oven-dried kerogen and the mass of the extracted kerogen as an amount of oil in the organic matter; and
  multiplying a ratio of the amount of oil in the organic matter to a weight of the second shale sample by 100 to obtain an amount of oil in the organic matter of the shale sample.

6. The method for detecting an amount of shale oil based on an occurrence state according to claim 5, wherein said determining an amount of oil in an inorganic mineral according to the total content of shale oil in the shale and the amount of oil in the organic matter of the shale sample specifically comprises:
  subtracting the amount of the oil in the organic matter of the shale sample from the total content of shale oil in the shale to obtain an amount of oil in the inorganic mineral of the shale sample;
  fitting a ratio of the amount of oil in the inorganic mineral of the shale sample to the amount of oil in the organic matter of the shale sample and parameters of the shale sample to establish a model for predicting the ratio of the amount of oil in the inorganic mineral of shale to the amount of oil in the organic matter, wherein the parameters of the shale sample comprise mineral composition ratios, total organic carbon (TOC), vitrinite reflectance (VR) and porosity;
  obtaining an amount of oil in an organic matter of shale to be detected; and
  using the prediction model to determine an amount of oil in an inorganic mineral of the shale to be detected according to the amount of oil in the organic matter of the shale to be detected;
  wherein, the prediction model is expressed by:

$$W_{inorganic/organic} = \frac{1}{\sqrt{2\pi} \cdot (d_1 + d_2)} (M_{TOC} \cdot TOC + M_q \cdot Quanrtz + M_c \cdot Clay + M_o \cdot Other) \cdot EXP\left[-\left(\frac{\ln R_o - a}{d_1}\right)^2 - \left(\frac{\ln \Phi - b}{d_2}\right)^2\right]$$

wherein $W_{inorganic/organic}$ indicates a ratio of the amount of oil in the inorganic mineral of the shale to the amount of oil in the organic matter of the shale sample; TOC indicates total organic carbon; $M_{TOC}$ indicates a TOC coefficient; Quartz indicates a quartz ratio; $M_q$ indicates a quartz ratio coefficient; Clay indicates a clay mineral ratio; $M_c$ indicates a clay mineral ratio coefficient; Other indicates other ratio, such as a carbonate mineral ratio; $M_o$ indicates other mineral ratio coefficient, such as a carbonate mineral ratio coefficient; $R_o$ indicates VR; a indicates a first VR coefficient; $d_1$ indicates a second VR coefficient; $\Phi$ indicates porosity; b indicates a first porosity coefficient; and $d_2$ indicates a second porosity coefficient.

7. The method for detecting an amount of shale oil based on an occurrence state according to claim 6, wherein said performing molecular dynamics simulation on the kaolinite pore-shale oil model to obtain a density curve of shale oil in the kaolinite pore specifically comprises:
  performing EM and relaxation on the kaolinite pore-shale oil model; and
  performing molecular dynamics simulation on the relaxed kaolinite pore-shale oil model by using the NPT ensemble at a preset temperature and pressure to obtain a density curve of shale oil in the kaolinite pore.

8. The method for detecting an amount of shale oil based on occurrence state according to claim 7, wherein said determining a surface oil adsorption capacity per unit area of kaolinite according to the density curve of shale oil in the kaolinite pore and a surface area of the kaolinite pore-shale oil model specifically comprises:
  determining a surface oil adsorption capacity per unit area of kaolinite according to the following formula:

$$c = (c_{ada-a} + c_{ads-a})/2$$

$$c_{ada-a} = \frac{m_{ada}}{A_{ada}} = \frac{\int_{L_5}^{L_6} s_{model}^{(1)} \cdot \rho_{oil}^{(1)} dL}{A_{ada}}$$

$$c_{ads-a} = \frac{m_{ads}}{A_{ads}} = \frac{\int_{L_7}^{L_8} s_{model}^{(1)} \cdot \rho_{oil}^{(1)} dL}{A_{ads}}$$

wherein c represents the surface oil absorption capacity per unit area of kaolinite; $C_{ada-a}$ represents a surface oil absorption capacity per unit area of an aluminum-oxygen octahedron; $C_{ads-a}$ represents a surface oil absorption capacity per unit area of a silicon-oxygen tetrahedron; $m_{ada}$ represents a surface adsorption mass of the aluminum-oxygen octahedron; $m_{ads}$ represents a surface adsorption mass of the silicon-oxygen tetrahedron; $A_{ada}$ represents a surface area of the aluminum-oxygen octahedron in the kaolinite pore-shale oil model; $A_{ads}$ represents a surface area of the silicon-oxygen tetrahedron in the kaolinite pore-shale oil model; $s_{model}^{(1)}$ represents a cross-sectional area of the kaolinite pore-shale oil model; $\rho_{oil}^{(1)}$ represents a density curve of shale oil in the kaolinite pore; $L_5$ represents an initial position of the density curve of shale oil in the kaolinite pore; $L_6$ represents a cut-off position of a surface adsorption layer of the aluminum-oxygen octahedron; $L_7$ represents a position where an adsorbed phase separates from a free phase on a surface of the aluminum-oxygen octahedron; and $L_8$ represents a cut-off position of the density curve of shale oil in the kaolinite pore.

9. A system for detecting an amount of shale oil based on an occurrence state, comprising:
  a kerogen swelled amount determination module, for obtaining a kerogen molecular model, loading the kerogen molecular model into a pore formed by a graphene lamellar structure, and performing EM, relaxation, simulated annealing and shale oil molecular loading in sequence to obtain a swelling and adsorption model of shale oil in kerogen; assigning a value to force fields of a shale oil molecule and a kerogen molecule in the kerogen shale oil swelling and adsorption model to determine kerogen and shale oil density curves; calculating a kerogen swelled amount according to the kerogen and shale oil density curves;

a kerogen adsorbed oil amount determination module, for determining an amount of adsorbed oil on a wall of kerogen according to a cross-sectional area of the kerogen shale oil swelling and adsorption model and the kerogen and shale oil density curves, and calculating an amount of kerogen adsorbed oil per unit area according to the amount of adsorbed oil on the wall of kerogen and the cross-sectional area; determining a specific surface area of kerogen according to a number and diameter of organic pores in a shale sample; multiplying the amount of kerogen adsorbed oil per unit area by the specific surface area of kerogen to obtain an amount of kerogen adsorbed oil;

an organic pore free oil amount determination module, for obtaining a kerogen swelling capacity and an organic pore volume formed by kerogen generated oil and gas, and calculating an organic pore volume corresponding to organic carbon according to the kerogen swelling capacity and the organic pore volume formed by kerogen generated oil and gas; multiplying a difference between the organic pore volume corresponding to the organic carbon and a volume of a kerogen adsorbed oil phase by a shale oil density, to obtain an amount of free oil in an organic pore, wherein the volume of the kerogen adsorbed oil phase is a ratio of the amount of kerogen adsorbed oil to a density thereof;

an inorganic mineral oil amount determination module, for dividing the shale sample into a first shale sample and a second shale sample, and extracting the first shale sample by using chloroform to obtain a total content of shale oil in the shale; sequentially enriching kerogen from the second shale sample, oven-drying, extracting with chloroform and comparing a mass of kerogen to obtain an amount of oil in an organic matter of the shale sample; determining an amount of oil in an inorganic mineral according to the total content of shale oil in the shale and the amount of oil in the organic matter of the shale sample;

an inorganic mineral adsorbed oil amount determination module, for loading compound composition of shale oil into a kaolinite pore to obtain a kaolinite pore-shale oil model, and performing molecular dynamics simulation on the kaolinite pore-shale oil model to obtain a density curve of shale oil in the kaolinite pore; determining a surface oil adsorption capacity per unit area of kaolinite according to the density curve of shale oil in the kaolinite pore and a surface area of the kaolinite pore-shale oil model; determining a specific surface area of the inorganic mineral in the shale sample according to a number of inorganic pores in the shale sample and a surface area of an inorganic pore in the shale sample; multiplying the surface oil adsorption capacity per unit area of kaolinite by the specific surface area of the inorganic mineral in the shale sample to obtain an amount of adsorbed oil by the inorganic mineral in the shale;

an inorganic pore free oil amount determination module, for determining a difference between the amount of oil in the inorganic mineral and the amount of adsorbed oil by the inorganic mineral in the shale as an amount of free oil in the inorganic pore; and a model establishment module, for establishing an occurrence-state-based shale oil quantification model according to the kerogen swelled amount, the amount of kerogen absorbed oil, the amount of free oil in the organic pore, the amount of adsorbed oil by the inorganic mineral and the amount of free oil in the inorganic pore, and detecting an amount of shale oil according to the occurrence-state-based shale oil quantification model;

wherein obtaining the kerogen molecular model, loading the kerogen molecular model into the pore formed by a graphene lamellar structure, and performing EM, relaxation, simulated annealing and shale oil molecular loading in sequence to obtain the swelling and adsorption model of shale oil in kerogen comprises:

loading the kerogen molecular model into a pore formed by a graphene lamellar structure, then performing EM, and performing relaxation at 75° C. under 20 MPa for 200 ps to obtain a compacted kerogen aggregate model;

subjecting the compacted kerogen aggregate model to 200 ps relaxation warming, and performing simulation by using a constant number of particles, pressure, and temperature (NPT) ensemble at 800° C. under normal pressure for 2 ns to obtain a kerogen slit pore; and loading a shale oil molecule into the kerogen slit pore to obtain a swelling and adsorption model of shale oil in kerogen.

* * * * *